United States Patent [19]

Hyman

[11] Patent Number: 5,436,143
[45] Date of Patent: Jul. 25, 1995

[54] METHOD FOR ENZYMATIC SYNTHESIS OF OLIGONUCLEOTIDES

[76] Inventor: Edward D. Hyman, 2100 Sawmill Rd., Apt. 4–103, River Ridge, La. 70123

[21] Appl. No.: 995,791
[22] Filed: Dec. 23, 1992
[51] Int. Cl.$^6$ ............................................. C12P 19/34
[52] U.S. Cl. ................... 435/91.2; 435/91.1; 435/91.21; 435/91.3; 435/91.31; 435/91.5; 435/91.51; 435/91.52; 536/24.33; 536/25.3; 536/25.31; 935/16; 935/88
[58] Field of Search ................... 435/91, 6, 91.1, 91.2, 435/91.21, 91.3, 91.31, 91.5, 91.51, 91.52; 536/25.3, 25.6, 24.33, 25.31; 935/16, 88

[56] References Cited

U.S. PATENT DOCUMENTS 3,850,749 11/1974 Kaufmann et al. .
4,661,450 4/1987 Kempe et al. ................ 435/172.3
4,987,071 1/1991 Cech et al. ........................ 435/91

OTHER PUBLICATIONS

Uhlenbeck et al. (1982) *The Enzymes*, vol. XV, pp. 31–58.
Hoffmann et al. (1987) Nucleic Acids Research, vol. 15, No. 3, pp. 5289–5303.
Shum et al., "Simplified method for large scale enzymatic synthesis of oligoribonucleotides", Nucleic Acids Res. 5: 2297–2311 (1978).
Schott et al., "Single-step elogation of oligodeoxynucleotides using terminal deoxynucleotidyl transferase", Eur. J. Biochem. 143: 613–620 (1984).
Mackey et al., "New approach to the synthesis of polyribonucleotides of defined sequence", Nature 233: 551–553 (1971).
Hinton et al., "The preparative synthesis of oligodeoxy-ribonucleotides using RNA ligase", Nucleic Acids Res. 10: 1877–1894 (1982).
England et al., "Dinucleotide pyrophosphates are substrates for T4-induced RNA ligase", Proc. Nat'l Acad Sci. (USA) 74: 4839–4842 (1977).
Beckett et al., "Enzymatic Synthesis of Oligoribonucleotides", in *Oligonucleotide Synthesis: A Practical Approach*, M. J. Gait ed., pp. 185–197 (1984).
Mudrakovskaya et al., "RNA Ligase of Bacteriophage T4. VII: A solid pahse enymatic synthesis of oligoribonucelotides", Biorg. Khim., 17: 819–822 (1991).
Stuart et al., "Synthesis and Properties of Oligodeoxynucleotides with an AP site at a preselected location", Nulceic Acids Res. 15: 7451–7462 (1987).
Norton et al., "A ribonuclease specific for 2'-O-Methyltaed Ribonulceic Acid", J. Biol. Chem. 242: 2029–2034 (1967).
Eckstein et al., "Phosphorothioates in molecular biology", TIBS 14:97–100 (1989).
Bryant et al., "Phosphorothioate Substrates for T4 RNA Ligase", Biochemistry 21: 5877–5885 (1982).
McLaughlin et al., "Donor Activation in the T$ RNA Ligase Reaction", Biochemistry 24: 267–273 (1985).
Ohtsuka et al., "A new method for 3'-labelling of polyribonucelotides by phosphorylation with RNA ligase and its application to the 3'-modification for joining reactions", Nulceic Acids Res. 6: 443–454 (1979).

(List continued on next page.)

*Primary Examiner*—Margaret Parr
*Assistant Examiner*—Ardin H. Marschel
*Attorney, Agent, or Firm*—Oppendahl & Larson

[57] ABSTRACT

Enzymatic synthesis of oligonucleotides may be performed in a single vessel without intermediate purification, by the steps of:

(a) combining a nucleotide primer sequence and a blocked nucleotide in the presence of a chain extending enzyme whereby a reaction mixture is formed containing the blocked nucleotide coupled to the nucleotide primer sequence at its 3' end;
(b) inactivating the chain extending enzyme;
(c) removing the blocking group from the primer-blocked nucleotide to form a primer-nucleotide product; and converting any unreacted blocked nucleotide to an unreactive form which is substantially less active as a substrate for the chain extending enzyme than the blocked nucleotide.

18 Claims, 7 Drawing Sheets

OTHER PUBLICATIONS

Kornberg, A., "Reversible Enzymatic Sysnthesis of Diphosphopyridine nucleotide and inorganic pyrophosphate", J Biol. Chem. 182: 779–793 (1950).

Kaplan et al., "Enzymatic Deamination of Adenosine Derivatives", J. Biol. Chem. 194: 579–591 (1952).

Bartkiewicz et al., "Nucleotide pyrophosphatase from potato tubers", Eur. J. Biochem. 143: 419–426 (1984).

Rand et al., "Sequence and cloning of bacteriophage T4 gene 63 encoding RNA ligase and tail fibre attachment activities", The EMBO Journal 3: 397–402 (1984).

Heaphy et al., "Effect of Single Amino Acid Changes in the Region of the Adenylation Site of T4 RNA IIgase", Biochemistry 26: 1688–1696 (1987).

Lowe et al., "Molecular cloning and expression of a cDNA encoding the membrane–associated rat intestinal alkaline phosphatase", Biochem. Biophys. Acta 1037: 170–177 (1990).

Chang et al., "Molecular Biology of Terminal Transferase", CRC Crit. Rev. Biochem. 21: 27–52.

Razzell et al., "Studies on Polynucleotides: III. Enzymatic Degradation. Substrate Specificity and Properties of Snake Venom Phosphodiesterase", J. Biol. Chem. 234: 2105–2113 (1959).

Tessier et al., "Ligation of Single-Stranded Oligodeoxyribonucleotides by T4 RNA Ligase", Analytical Biochemistry 158: 171–178 (1986).

England et al., "Enzymatic Oligoribonucleotide Synthesis with T4 RNA Ligase", Biochemistry 17: 2069–2076 (1978).

Middleton et al., "Synthesis and Purification of Oligonucleotides Using T4 RNA Ligase and Reverse-Phase Chromatography", Analytical Biochemistry 144: 110–117 (1985).

Soltis et al., "Independent Locations of Kinase and 3'-Phosphatase Activities on T4 Polynucleotide Kinase", J. Biol. Chem. 257: 11340–11345 (1982).

Apostol et al., "Deletion Analysis of a Multifunctional yeast tRNA Ligase Polypeptide", J. Biol. Chem/ 266: 7445–7455 (1991).

Becker et al., "The Enzymatic Cleavage of Phosphate Termini from Polynucleotides", J. Biol. Chem. 242: 936–950 (1967).

Greer et al., "RNA Ligase in Bacteria: Formation of a 2',5' Linkage by an *E. coli* Extract", Cell 33: 899–906 (1983).

Schwartz et al., "Enzymatic Mechanism of an RNA Ligase from Wheat Germ", J. Biol. Chem. 258: 8374–8383 (1983).

Beabealashvilli, et al., "Nucleoside 5'-triphosphates modified at sugar residues as substrates for calf thymus terminal deoxynucleotidyl transferase and for AMV reverse transcriptase", Biochim. Biophys. Acta 868: 136–144 (1986).

Lehman et al., "The Deoxyribonucelases of *Escherichia coli*", J. Biol. Chem. 239: 2628–2636 (1964).

UNCONTROLLED METHOD
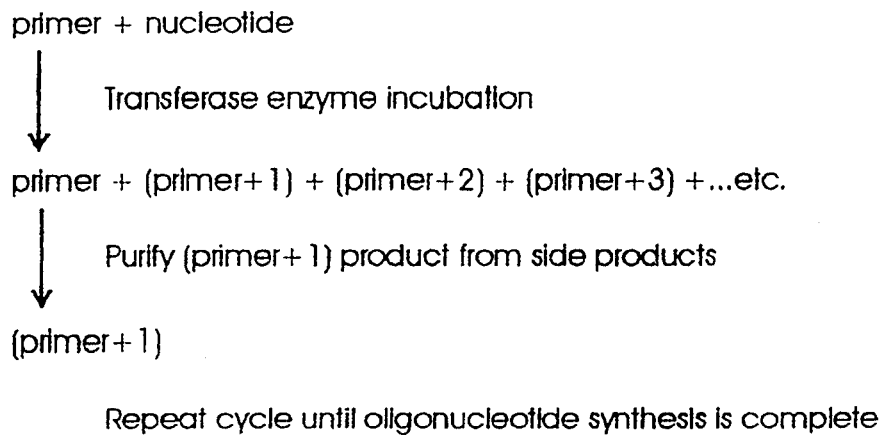
BLOCKED METHOD
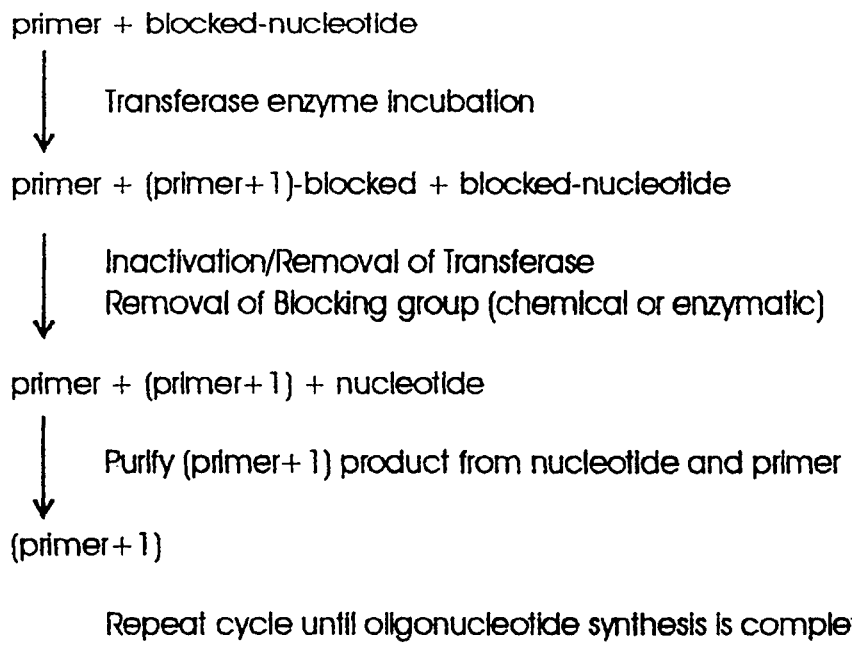
FIGURE 1

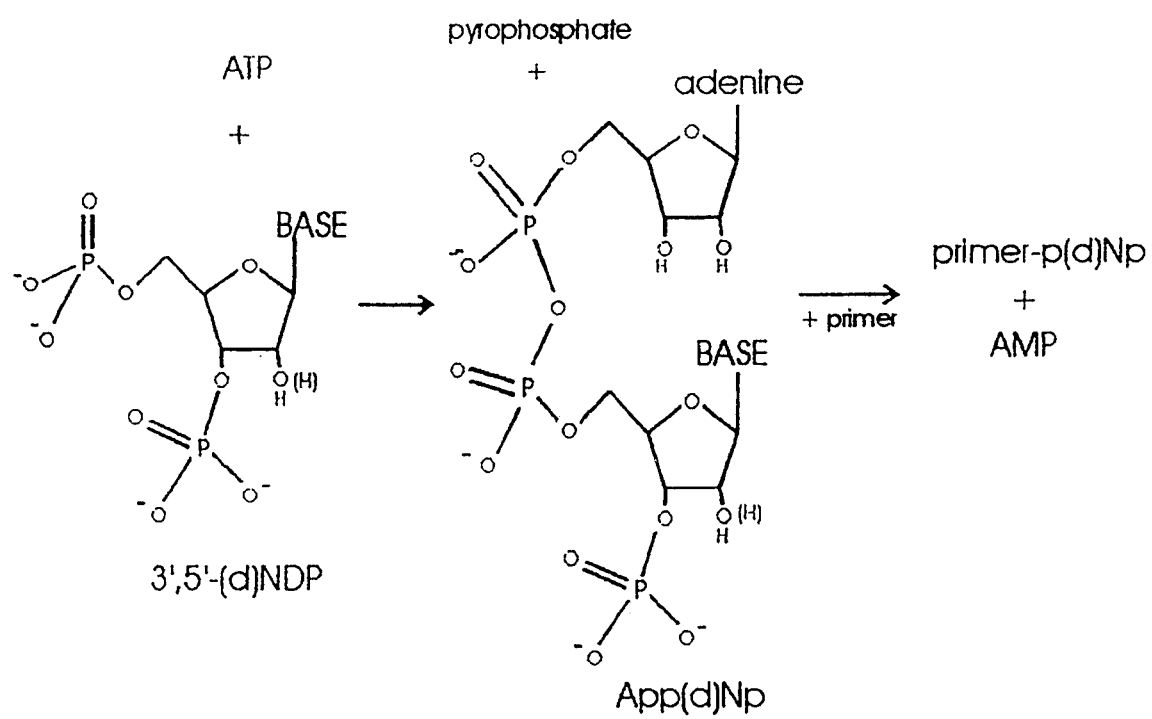
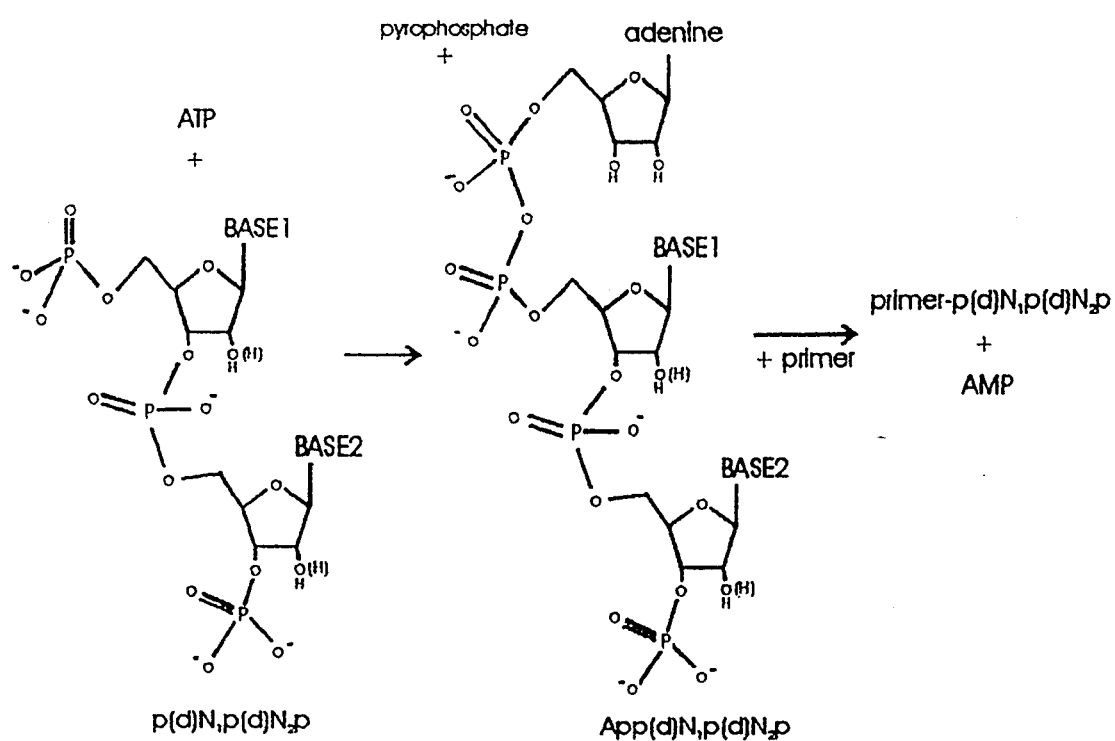
FIGURE 4 primer + App(d)Np (or ATP + 3', 5'-(d)NDP)

↓ Pump through RNA Ligase Column, recirculate if necessary
Heat Inactivation of trace RNA Ligase leaked into solution (if necessary)

primer + primer-(d)Np + App(d)Np + AMP

↓ Pump through Exonuclease + Nucleotide Pyrophosphatase Column
(e.g. snake venom PDE I), recirculate if necessary
Heat Inactivation of trace Exonuclease and Nucleotide Pyrophosphatase leaked into solution (if necessary)

primer-(d)Np + 3', 5'-(d)NDP + AMP + (d)NMP's

↓ Pump through Alkaline Phosphatase Column, recirculate if necessary
Heat Inactivation of trace Alkaline Phosphatase leaked into solution (if necessary)

primer-(d)N + (deoxy)nucleosides + adenosine + $PO_4$

Repeat cycle until oligonucleotide synthesis is complete

FIGURE 6

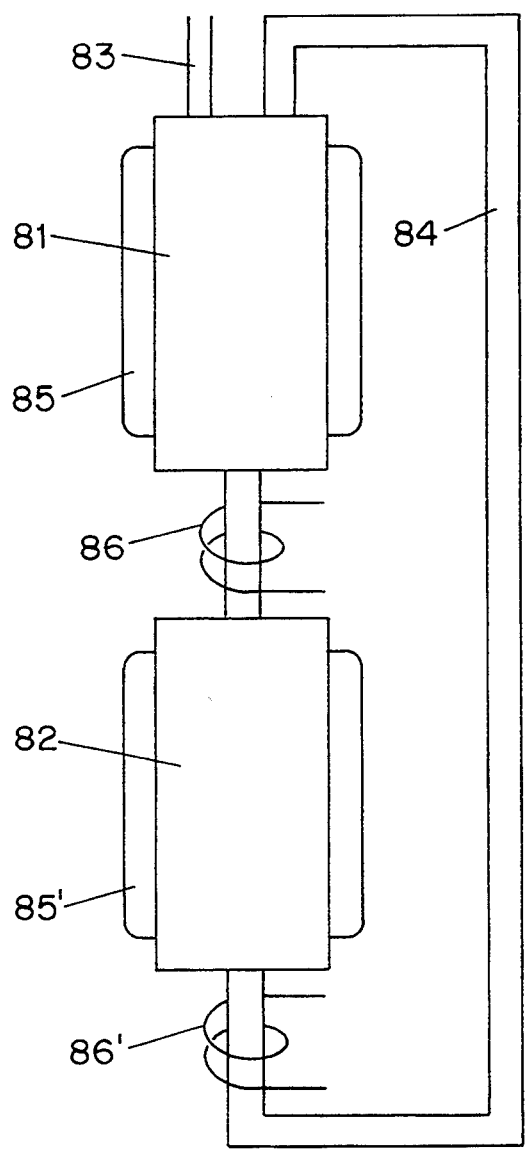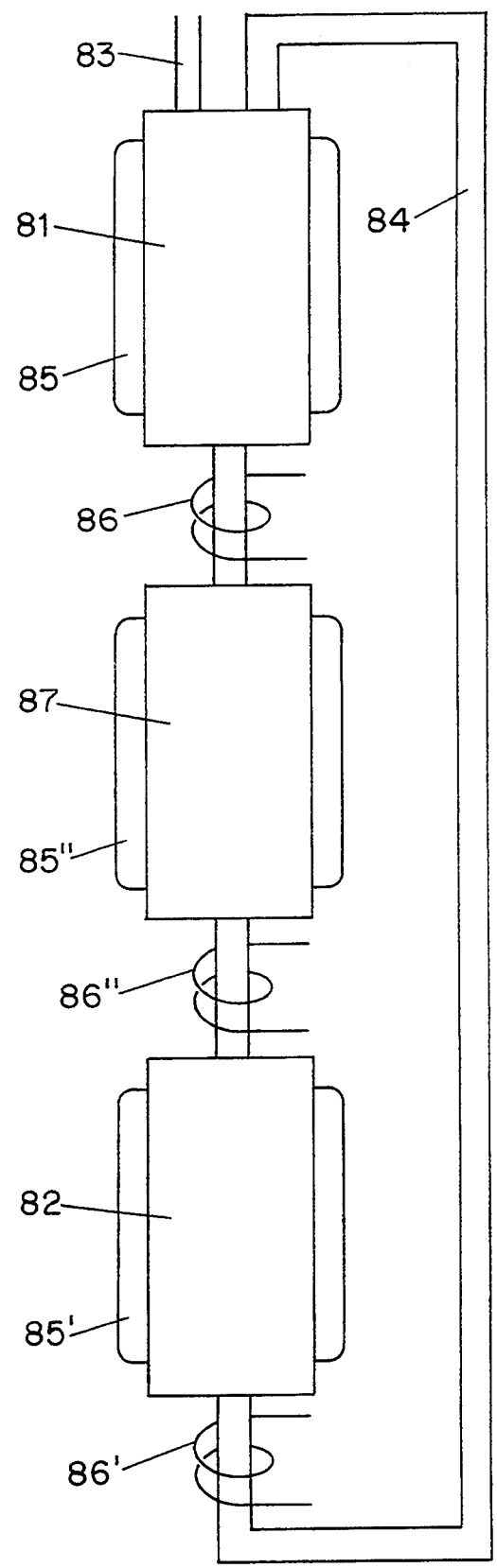
FIGURE 8A
FIGURE 8B

METHOD FOR ENZYMATIC SYNTHESIS OF OLIGONUCLEOTIDES

BACKGROUND OF THE INVENTION

Synthetic oligonucleotides play a key role in molecular biology research, useful especially for DNA sequencing, DNA amplification, and hybridization. A novel "one pot" enzymatic method is described to replace both the obsolete enzymatic methods and the current phosphoramidite chemical method. This new method promises increased throughput and reliability, ease of automation, and lower cost.

Before the introduction of the phosphoramidite chemical method in 1983, enzymatic methods were used for the synthesis of oligonucleotides. Historically, two distinct enzymatic approaches have been employed as summarized in FIG. 1. These enzymatic methods have been abandoned, however, in favor of the superior phosphoramidite chemical method.

The first enzymatic approach is the "uncontrolled" method. As depicted in FIG. 1, a short oligonucleotide primer is incubated with the desired nucleotide and a nucleotidyl transferase. At the end of the optimal incubation period, a mixture of oligonucleotide products containing different numbers of bases added to the primer (i.e. primer, primer +1, primer +2 . . . ) is obtained. The desired product, the primer with one added base, is purified using either electrophoresis or chromatography. The process of enzyme incubation and oligonucleotide purification is repeated until the desired oligonucleotide is synthesized. Examples of the use of this approach are: (1) Polynucleotide Phosphorylase ("PNP") and ADP, GDP, CDP, and UDP have been used to make oligoribonucleotides in accordance with the following reaction:

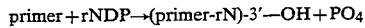
primer+rNDP→(primer-rN)-3'—OH+PO4

(B. W. Shum et al, *Nucleic Acids Research*, (1978), 5(7), 2297–311), and (2) Terminal deoxynucleotidyl Transferase ("TdT") and the nucleotides dATP, dGTP, dCTP, and dTTP have been used to make oligodeoxyribonucleotides in accordance with the following reaction:

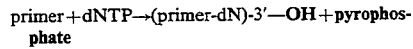
primer+dNTP→(primer-dN)-3'—OH+pyrophosphate (H. Schott et al, *Eur. J. Biochem*, (1984), 143, 613–20). The flaws of the "uncontrolled" approach are the requirement for cumbersome manual purification of the oligo+1 product after each coupling cycle, poor yields of the desired oligo+1 product, and inability to automate.

The second enzymatic approach is the "blocked" method, also shown in FIG. 1. The nucleotide used in the extension step is blocked in some manner to prevent the nucleotidyl transferase from adding additional nucleotides to the oligonucleotide primer. After the extension step, the oligonucleotide product is separated from the enzyme and nucleotide, and the blocking group is removed by altering the chemical conditions or by the use of a second enzyme. The oligonucleotide product is now ready for the next extension reaction. Examples of this approach are: (1) PNP and NDP-2'-acetal blocked nucleotides have been used to make oligoribonucleotides. The acetal blocking group is removed under acidic conditions (P. T. Gilham et al, *Nature*, (1971), 233, 551-3 and U.S. Pat. No. 3,850,749), (2) RNA ligase and the blocked nucleotide App(d)Np (or ATP+3',5'-(d)NDP) have been used to make oligoribonucleotides and oligodeoxyribonucleotides. The 3'-phosphate blocking group is removed enzymatically with a phosphatase such as alkaline phosphatase (T. E. England et al, *Biochemistry*, (1978), 17(11), 2069–81; D. M. Hinton et al, *Nucleic Acids Research*, (1982), 10(6), 1877–94).

The advantage of the "blocked" method over the "uncontrolled" method is that only one nucleotide can be added to the primer. Unfortunately, the "blocked" method has several flaws which led to its abandonment in favor of the chemical method. The "blocked method", like the "uncontrolled" method, requires the purification of the oligonucleotide product from the reaction components after each coupling cycle.

In the first approach, using PNP, the oligonucleotide is exposed to acid to remove the acid-labile acetal blocking group. Oligonucleotide product must be purified and redissolved in fresh buffer in preparation for the next polymerization reaction for two reasons: (1) PNP requires near neutral pH conditions whereas acetal removal requires approximately pH 1; and (2) the product of the polymerization reaction, PO4, must be removed or it will cause phosphorolysis of the oligoribonucleotide catalyzed by PNP.

In the second approach, using RNA ligase, the art teaches that oligonucleotide product needs to be purified after each cycle because the dinucleotide App(d)N, formed by phosphatase treatment of App(d)Np, is still a suitable substrate for RNA ligase and must be completely removed prior to addition of RNA ligase in the next cycle (T. E. England et al., *Proc. Natl. Acad. Sci. USA*, (1977), 74(11), 4839–42). Hinton et al. emphasize the importance of purifying oligonucleotide product after each cycle by stating: "This elution profile [a DEAE-sephadex chromatogram of oligodeoxyribonucleotide product] also demonstrates the absence of either significant contaminating products arising from nucleases or of the reaction intermediate, A-5'pp5'-dUp. The absence of such substances is critical if this general methodology is to be useful for synthesis."(D. M. Hinton et al, *Nucleic Acids Research*, (1982), 10(6), 1877–94).

Two modifications have been devised for the "blocked" method to improve the oligonucleotide product yield and to speed required oligonucleotide product purification after each coupling cycle. The first modification was the use of a branched synthetic approach (Oligonucleotide Synthesis: a practical approach, M. J. Gait editor, (1985), pp. 185–97, IRL Press). This approach improved the yield of final oligonucleotide product, but intermediate purification of oligonucleotide after each coupling cycle was still required. The second modification was the covalent attachment of the primer chain to a solid phase support (A. V. Mudrakovskaia et al, *Bioorg Khim*, (1991), 17(6), 819–22). This allows the oligonucleotide to be purified from all reaction components simply by washing the solid phase support column. This latter modification provides facile purification of oligonucleotide product after each polymerization cycle, but product yields are still low, and primer chains which do not couple during a cycle are not removed and are carried over to the next coupling cycle. It appears that the poor coupling efficiency results from steric problems encountered by the enzyme in gaining access to the covalently bound primer chain. Unfortunately, it is not possible to combine these two modifications in an automated manner.

In fact, the current phosphoramidite chemical method for oligonucleotide synthesis utilizes a solid phase support to facilitate oligonucleotide purification after each coupling reaction. The reason for the success of this chemical method is that the coupling efficiency is high, 95% to 99%, and oligonucleotides which fail to couple in a cycle can be capped with acetic anhydride, preventing the accumulation of n−1 failure sequences.

It is an object of the present invention to provide a method for enzymatic oligonucleotide synthesis which can preferably be performed entirely in a single tube, requiring only temperature control and liquid additions, without requiring intermediate purifications or any other manipulation. Such a method would be well suited for a commercial liquid handling robot to prepare several hundred oligonucleotides per day in microtiter plates. This technology would not be hindered by the need for solid phase support columns, which severely complicates instrument construction and severely limits the number of oligonucleotides which can be made simultaneously per day. Currently, the best commercially available instruments which automate the phosphoramidite method can prepare only four oligonucleotides simultaneously on four solid phase columns in several hours (Applied Biosystems, Inc.).

SUMMARY OF THE INVENTION

This invention provides a method for enzymatic synthesis of oligonucleotides. The method, which may advantageously be performed in a single vessel without intermediate purification, involves the steps of:

(a) combining a nucleotide primer sequence and a blocked nucleotide in the presence of a chain extending enzyme whereby a reaction mixture is formed containing the blocked nucleotide coupled to the nucleotide primer sequence at its 3' end;

(b) inactivating the chain extending enzyme;

(c) removing the blocking group from the primer-blocked nucleotide to form a primer-nucleotide product; and (d) converting any unreacted blocked nucleotide to an unreactive form which is substantially less active as a substrate for the chain extending enzyme than the blocked nucleotide.

These steps are then repeated, preferably in the same pot, and without intermediate purification of oligonucleotide product, until the desired base sequence is synthesized. The removal of the blocking group and the conversion of unreacted blocked nucleotide to an unreactive form is preferably performed using an enzyme or combination of enzymes. In this case, the enzyme or enzyme combination is inactivated at the end of each cycle.

In accordance with one embodiment, a single cycle of the method consists of the steps in sequence:

(a) incubation of an oligonucleotide primer with RNA ligase and App(d)Np or App(d)N$_1$p(d)N$_2$p or precursors thereof;

(b) heat inactivation of RNA ligase;

(c) incubation with Phosphatase; and (d) heat inactivation of the Phosphatase;

In accordance with a preferred embodiment, a single cycle of the method consists of the steps in sequence:

(a) incubation of an oligonucleotide primer with RNA ligase and App(d)Np or App(d)N$_1$p(d)N$_2$p or precursors thereof;

(b) heat inactivation of RNA ligase;

(c) incubation with Exonuclease and Nucleotide Pyrophosphatase (e.g. Snake Venom Phosphodiesterase I);

(d) heat inactivation of the Exonuclease and Nucleotide Pyrophosphatase;

(e) incubation with Phosphatase; and (f) heat inactivation of the Phosphatase.

The invention also includes an apparatus for performing the method of the invention. This apparatus includes:

at least one vessel for performing synthesis of an oligonucleotide;

means for separately supplying at least four different blocked nucleotide feed stocks;

means for supplying at least two different enzyme preparations, i.e., the first and second enzymes referred to above;

means for inactivating the enzymes; and means for controlling the sequential addition of reagents, incubation and inactivation steps of the claimed method.

BRIEF DESCRIPTION OF THE DRAWINGS

FIG. 1: The "Uncontrolled" and "Blocked" enzymatic methods previously used for the synthesis of oligonucleotides. Both methods require purification of oligonucleotide product after each coupling cycle.

FIG. 4: Reactions catalyzed by RNA ligase relevant to the One Pot enzymatic method. Phosphorothioate derivatives are indicated in parenthesis.

FIG. 6: Enzyme Column Technique for performing the method of the Invention.

FIG. 8A–8B: Automated instrument for the synthesis of oligonucleotides using the Enzyme Column Technique.

DETAILED DESCRIPTION OF THE INVENTION

The present invention provides a method for synthesizing oligonucleotides enzymatically that can be performed in a single vessel without the need for intermediate purification steps. A simple embodiment of the method of the invention is shown in FIG. 2.

Figure 2:
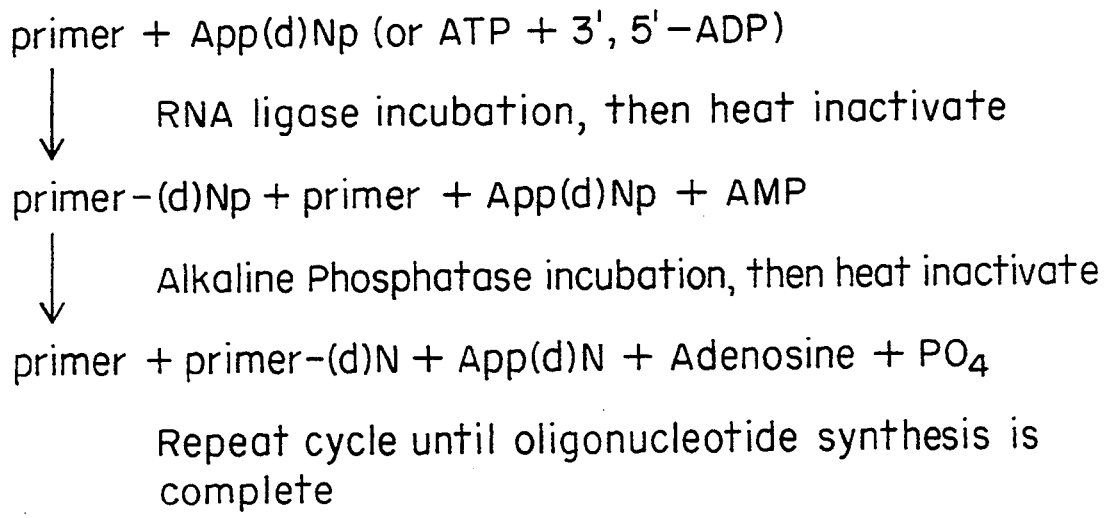
FIG. 2: The Basic One Pot enzymatic method for the synthesis of oligonucleotides. This method obviates the need for intermediate purification of oligonucleotides and for removal of unreacted nucleotides.

As shown in FIG. 2, a reaction mixture is formed containing a primer and a blocked nucleotide substrate for a chain extending enzyme such as RNA ligase and is incubated in the presence of the enzyme to couple the primer chain with the blocked nucleotide. The RNA ligase is then inactivated, for example by heating. The resulting reaction mixture contains the primer/blocked nucleotide product, unreacted primer, unreacted blocked nucleotide, and adenosine monophosphate (AMP).

The next step as shown in FIG. 2 is incubation with an enzyme which removes the blocking group from the coupled and uncoupled blocked nucleotide. When synthesizing relatively short oligonucleotides, i.e., up to 25 additional bases added to the primer, the resulting reaction mixture, containing unreacted primer, extended primer, unblocked nucleotide substrate and nucleotide degradation products can then be recycled directly for use as the primer in subsequent cycles without intermediate purification being required because the blocked nucleotide is substantially more active as a substrate for RNA ligase (e.g. 50 to 100 times more active) than the unblocked nucleotide. If longer oligonucleotides are to be synthesized, additional steps may be added to the method to substantially reduce or eliminate the activity of the unreacted nucleotide from previous cycles as a substrate for the chain extending enzyme.

After the completion of the appropriate number of cycles, the synthesized oligonucleotide is recovered from the reaction mixture. Recovery of the synthesized oligonucleotide can be accomplished by standard methods: extraction with organic solvents such as phenol, chloroform and ethyl ether to remove proteins and peptides; precipitation, e.g. using ethanol or isopropanol in the presence of high salt concentration followed by centrifugation to collect the precipitate; size exclusion chromatography, e.g. SEPHADEX G-10 spun column chromatography; anion exchange chromatography; reverse phase chromatography; thin layer chromatography, e.g. using cellulose, polyethyleneimine cellulose or silica gel; ultrafiltration or dialysis using a small pore membrane; gel electrophoresis, e.g. using urea polyacrylamide or agarose gels; hybridization to complementary nucleotide probes; or affinity ligand interaction to an affinity label such as biotin attached to the original primer or one of the incorporated bases. The oligonucleotide may also be attached to a solid support throughout its synthesis, e.g., via the primer, in which case final purification is a simple matter of washing the support.

Primers

The initial primer used in the method of the invention is an oligonucleotide having a length of at least three bases, which can be extended by the chain extending enzyme employed, e.g., RNA ligase. The primer may be selected to provide the first three bases of the ultimate product, or it may be selected to provide facile cleavage to yield the desired ultimate product.

Primers for use in the invention can be made using known chemical methods, including the phosphoramidite method. Other methods include DNase or RNase degradation of synthetic or naturally occurring DNA or RNA. Numerous primers suitable for use in the invention are commercially available from a variety of sources.

In most applications, the presence in the oligonucleotide product of the 5' extension corresponding to the initial primer is inconsequential. These applications may include DNA sequencing, polymerase chain reaction, and hybridization. However, some applications may necessitate the removal of this 5' extension. Several procedures have been designed to achieve this result. All procedures are based on the general principle of selective enzymatic cleavage of the initial primer, without digestion of the synthesized oligonucleotide. This is accomplished by structural or sequence differences in the initial and synthesized oligonucleotides, and by the use of enzymes which can detect such differences. All procedures for removing the initial primer are performed in accordance with the one pot concept, by requiring only additions to the oligonucleotide solution. Thus, a liquid handling robot can also perform the initial primer cleavage using only reagent additions, and without manual intervention.

The following summarizes these procedures, categorized by the type of synthesized oligonucleotide for which a procedure can be used: oligodeoxyribonucleotides, oligoribonucleotides, and both types.

Oligodeoxyribonucleotides (1) Initial primers containing a 3' terminal ribose can be cleaved with either RNase or alkali. RNase specifically recognizes and hydrolyzes at the ribose bases of an oligonucleotide. Many RNases are available with different specificities. For example, RNase A cleaves at the 3' side of only cytidine and uridine bases; therefore, the terminal ribose of the initial primer should be either a cytidine or uridine base. RNase One (Promega) cleaves at all four bases; therefore, all four bases can be used as the terminal ribose. Mild alkali specifically cleaves RNA due to the vicinal diol arrangement of ribose. Therefore, addition of alkali can be used to specifically remove the initial primer. If the initial primer is composed entirely of ribose, RNase or alkali will completely hydrolyze this initial primer to 3'-NMP's or 2'-NMP's+3'-NMP's respectively. The desired oligonucleotide product will then be the only oligonucleotide in the tube. Alkaline cleavage has the advantage of removing any acetyl protecting groups on the bases if necessary; RNase cleavage has the advantage of working in neutral pH conditions, a necessity if the oligonucleotide product is unstable at high pH.

(2) Initial primers containing a 3' terminal deoxyuridine base can be cleaved by sequential treatment with Uracil DNA Glycosylase, followed by base catalyzed beta elimination (G. R. Stuart et al, *Nucleic Acids Research*, (1987), 15(18), 7451–62). The synthesized oligonucleotide will be phosphorylated at the 5' end after cleavage from the initial primer. This reaction is summarized below:

d(primer)-p-dU-p-d(oligo)+Uracil DNA
Glycosylase→d(primer)-p-deoxyribose-p-
d(oligo)alkaline
treatment→d(primer)-p-dehydroribose+

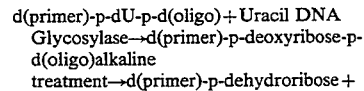

Oligiribonucleotides (1) Initial primers containing a 3' terminal deoxyribose base can be cleaved with DNase. Examples of RNase-free DNases include DNase I and DNase II.

Oligodeoxyribonucleotides and Oligoribonucleotides (1) If the initial primer contains the recognition sequence for a ribozyme and the synthesized oligonucleotide does not contain this recognition sequence, then the initial primer can be cleaved from the synthesized oligonucleotide by incubation with the ribozyme. Ribozymes are commercially available from US Biochemicals. Fortuitously, ribozymes cut at the 3' end of a four base recognition sequence 5'-CUCU-3'. Ribozymes with different recognition sites can be made by altering the base sequence of the ribozyme. Therefore, if an oligonucleotide contains the recognition site for one ribozyme, another ribozyme can be selected.

Alternatively, the initial primer can itself be a ribozyme containing the ribozyme recognition sequence. After synthesis of the oligonucleotide is complete, the synthesized oligonucleotide can be cleaved by adjusting reaction conditions to turn on the dormant ribozyme activity. Such changes in the reaction conditions include the addition of the essential ribozyme cofactor GTP or the addition of activators such as urea. The general problem with using ribozymes is that a guanosine base is introduced at the 5' end of the cleaved, synthesized oligonucleotide. Thus, a ribozyme can shorten the 5' extension to one guanosine base.

(2) If the initial primer contains the recognition sequence for a restriction endonuclease which is able to cleave single stranded DNA, and the synthesized oligonucleotide does not contain this recognition sequence, then the initial primer can be cleaved from the synthesized oligonucleotide by incubation with this restriction endonuclease. Examples of such single strand recognizing restriction endonucleases include Hha I, HinP I, MnI I, Hae III, BstN I, Dde I, Hga I, Hinf I, and Taq I (New England Biolabs catalog).

(3) If the initial primer contains a 3'-terminal modified sugar 2'-O-methyl ribose, and the synthesized oligonucleotide does not contain this modified sugar, then the initial primer can be cleaved from the synthesized oligonucleotide by incubation with RNase alpha, (J. Norton et al, *Journal of Biological Chemistry*, (1967), 242(9), 2029–34). This enzyme cuts only at bases in which the ribose sugar contains a 2'-O-methyl group.

(4) If the initial primer is composed of some ribose bases, an oligodeoxyribonucleotide specifically annealing to the initial primer and RNase H can be added to cleave the initial primer. RNase H is an enzyme which specifically hydrolyzes the RNA strand of a DNA-RNA hybrid.

(5) If the initial primer is composed of some ribose bases, an oligoribonucleotide specifically annealing to the initial primer and a double strand specific RNase such as RNase V1 can be added to cleave the initial primer. If the initial primer is a self-annealing oligoribonucleotide, which forms double stranded RNA, addition of an annealing oligoribonucleotide would not be necessary.

(6) An oligodeoxyribonucleotide is added which specifically anneals to the initial primer and forms double stranded DNA region recognition site for a restriction endonuclease. The initial primer is cleaved by addition of the restriction enzyme. The initial primer can also be a self-annealing oligodeoxyribonucleotide, which forms a double stranded DNA region containing the recognition site for a restriction endonuclease, obviating the need to add an annealing oligodeoxyribonucleotide.

(7) If the synthesized oligonucleotide contains phosphorothioate internucleotidic linkages, and the initial primer does not contain phosphorothioate internucleotidic linkages, then the initial primer can be cleaved by incubation with a nuclease which is unable to hydrolyze phosphorothioate internucleotidic linkages, or hydrolyzes them poorly. Using this procedure, the first base added to the initial primer should contain a normal phosphodiester linkage, allowing this base to become the 5' end of the released synthesized oligonucleotide. Subsequent bases added should contain phosphorothioate internucleotidic linkages. Examples of such nucleases include S1 nuclease, P1 nuclease, RNase, DNase I, DNase II, T5 exonuclease, phage SP3 exonuclease, exonuclease V, exonuclease VII, lambda exonuclease, staphylococcal nuclease, DNA Polymerase (5' to 3' exonuclease), and Phosphodiesterase II (F. Eckstein et al, Trends in *Biochemical Sci.*, (1989), 14, 97–100). Notice that these enzymes are either endonucleases or 5' to 3' exonucleases. If a 5' to 3' exonuclease is used, only one phosphorothioate linkage at the 5' end may be needed to protect all the phosphodiester linkages from digestion. Phosphorothioate internucleotidic linkages can be subsequently converted into phosphate linkages by desulfurization with a reagent such as 2-iodoethanol.

(8) If the initial primer contains a ribose base recognized by a base-specific Ribonuclease, and the synthesized oligonucleotide does not contain this ribose base, then the initial primer can be cleaved from the synthesized oligonucleotide by incubation with this base-specific Ribonuclease. There are several RNases which cleave at the 3' side of a single base. Examples include RNase $CL_3$ (cleaves after cytosine only), RNase $T_1$ (cleaves after guanosine only), and RNase $U_2$ (cleaves after adenosine only). This technique is best applied to synthesized oligonucleotides which contain only three of the four bases. However, the technique can be applied to all oligonucleotides if the base used the synthesized oligonucleotide is a base analog with similar base pairing properties, but which is resistant to the RNase cleavage. Alternatively, susceptible bases in the synthesized oligonucleotide may be protected using a phosphorothioate internucleotidic linkage, which is resistant to base-specific RNase cleavage.

A final step can be performed after cleavage of the initial primer from the synthesized oligonucleotide to selectively degrade the initial primer to nucleosides or nucleotides. This technique is based on the differential presence of a phosphate monoester at the 5' or 3' end of the initial primer and synthesized oligonucleotide and the use of differential digestion with an appropriate exonuclease. Three techniques are available depending on the prior cleavage procedure employed.

If the cleavage of the initial primer from the synthesized oligonucleotide results in a 5'-phosphate on the synthesized oligonucleotide, then subsequent incubation with spleen phosphodiesterase II (a 5' to 3' exonuclease) will selectively hydrolyze the initial primer (which has a 5' hydroxyl) to nucleotides, without hydrolyzing the synthesized oligonucleotide because of the enzyme's substantial preference for substrates with a terminal 5'-hydroxyl. The 5'-phosphate protects the synthesized oligonucleotide from hydrolysis. The pH may have to be lowered from the original synthetic conditions because phosphodiesterase II has an acidic optimum pH.

If the cleavage of the initial primer from the synthesized oligonucleotide results in a 3'-hydroxyl group on the cleaved initial primer (and thus usually a 5'-phosphate group on the synthesized oligonucleotide), the cleaved primer can be degraded prior to the removal of the 3-phosphate group from the synthesized oligonucleotide using a 3' to 5' exonuclease. Suitable exonucleases include exonuclease I, phosphodiesterase I and polynucleotide phosphorylase+$PO_4$ because of their substantial preference for 3'-hydroxyl as opposed to 3'-phosphate substrates.

If the cleavage of the initial primer will result in the formation of a synthesized oligonucleotide with a 5'-hydroxyl group and a 3'-phosphate group, the following protocol may be used. First, the primer-synthesized oligonucleotide is phosphorylated at the 5' end prior to cleavage, e.g., using ATP and phosphatase-free polynucleotide kinase, to ensure that the cleaved initial primer will have a 5'-phosphate group. Preferential degradation of the cleaved initial primer can then be accomplished using lambda exonuclease, a 5' to 3' exonuclease with a substantial preference for 5'-phosphate substrates.

The cleavage and digestion of the initial primer are favorably performed at the end of the synthesis; however, it can be performed after synthesizing the first three bases of the oligonucleotide.

Chain Extending Enzyme

The chain extending enzyme used in the method of the invention is preferably RNA ligase. RNA ligase is commercially available from New England Biolabs and has been well characterized in the literature. The reaction catalyzed by RNA ligase is shown in FIG. 4.

RNA ligase possesses a number of properties which make it particularly useful in the invention:

(1) The coupling reaction catalyzed by RNA ligase is highly favorable thermodynamically; a phosphoanhydride bond is broken, and a more stable phosphoester bond is formed. In the presence of the AMP degrading enzyme 5'-Nucleotidase, the coupling reaction is irreversible.

(2) RNA ligase readily polymerizes a multitude of nucleoside analogs, allowing the facile synthesis of oligonucleotides containing these analogs without modification of the One Pot protocol. These modified nucleotides include base analogs, sugar analogs, and, phosphorothioate analogs (O. C. Uhlenbeck et al, *The Enzymes*, (1982), volume XV, pp. 31–58, Academic Press and F. R. Bryant et al, *Biochemistry*, (1982), 21, 5877–85). This property is useful if acetylated bases are needed to prevent oligonucleotides from self-annealing. Such acetyl protecting groups can be cleaved with alkali.

(3) RNA ligase can couple both ribose and deoxyribose nucleotides, allowing the synthesis of oligodeoxyribonucleotides, oligoribonucleotides, and mixed ribose/deoxyribose oligonucleotides.

(4) Nucleotide donor substrates can be up to two bases in length for application in the method of the invention; i.e., p(d)Np(d)Np+ATP or the activated substrate App(d)Np(d)Np. Thus, the synthesis can proceed at a rate of two bases per coupling cycle. The basis for the success of this approach is that the unblocked dinucleotide p(d)Np(d)N-3'—OH cannot serve as a primer, since RNA ligase has a minimum primer length requirement of 3 bases. This p(d)Np(d)N-3'—OH unblocked dinucleotide is degraded by Exonuclease and Alkaline Phosphatase to nucleosides.

(5) The One Pot enzymatic method works in a mild aqueous environment. The specificity of the enzymatic reactions obviates the need for base protecting groups and highly reactive functional groups. All nucleotides and enzymes are stable for long periods in aqueous solution. All nucleotides used in the coupling reactions are stable at 95° C. for many hours. No hazardous and expensive organic solvents are needed. This is contrasted with the phosphoramidite chemical method which suffers the inconveniences of hazardous and expensive organic solvents and unstable nucleotides which are rapidly degraded by traces of water.

Blocked Nucleotides

The blocked nucleotide substrate employed in the initial step of the method of the invention is selected for compatibility with the chain extending enzyme. In the case of RNA ligase, the substrate may be an activated 2'- or 3'-blocked adenosine diphosphate-nucleotide or deoxynucleotide (e.g., App(d)Np or a precursor thereof, ATP 3'5'-(d)NDP). (See FIG. 4). The blocked nucleotide substrate may also be a dinucleotide such as p(d)Np(d)Np or App(d)Np(d)Np.

The choice of RNA ligase substrate influences the course of the reaction, as can be seen from a consideration of the following reaction mechanism:

(1) E+ATP⇌E-AMP+pyrophosphate
(2) E-AMP+3',5'-(d)NDP⇌E[App(d)Np]
(3) E[App(d)Np]+primer-3'—OH⇌(primer-(d)N)-3'-phosphate+AMp+E The use of unactivated nucleotides results in a short lag period in the coupling reaction in which the concentration of App(d)Np must build up to sufficient levels in solution before step 3 can occur. The mechanistic reason for this lag period is that the E[App(d)Np] complex rapidly dissociates before the enzyme can bind to primer. The use of activated nucleotide substrates avoids this lag period, allowing step 3 to occur instantly. Therefore, faster and more reliable RNA ligase coupling can be achieved using activated nucleotide substrates.

One interesting aspect of this reaction mechanism is that the mechanism in steps 1 and 2 uses an enzyme (RNA ligase) covalently modified by adenylylation. It is well documented in the scientific literature that the adenylylated enzyme is unable to catalyze step 3 of the reaction. This explains why the presence of ATP is inhibitory to the coupling reaction of step 3, by forming the adenylylated enzyme (step 1) which prevents the catalysis of step 3. Past investigators who have used RNA ligase for the synthesis of oligonucleotides have generally observed slow coupling rates and low coupling efficiencies, using either activated or unactivated nucleotide substrates. Although activated nucleotide substrates are well documented in the literature to have faster coupling rates, these coupling rates and coupling efficiencies are significantly lower than that observed in this invention. The error which researchers have consistently committed is the use of purified preparations of activated nucleotide substrate, e.g. App(d)Np which is prepared chemically or enzymatically with subsequent chromatographic purification (P. U. Hoffmann et al, *Nucleic Acids Research*, (1987), 15(13), 5289–303 and L. W. McLaughlin et al, *Biochemistry*, (1985), 24, 267–73). The error is revealed by examining step 2. The reverse reaction in step 2 occurs slowly, and the enzyme is irreversibly inactivated by adenylylation because no 3', 5'-(d)NDP is present to regenerate free enzyme. Researchers have circumvented this problem in the past by using large quantities of RNA ligase.

An alternative provided in accordance with the method of the invention is the addition of a small amount of 3',5'-(d)NDP, when using activated nucleotide substrates App(d)Np, to prevent RNA ligase from being irreversibly inactivated. E-AMP is rapidly converted to App(d)Np+free enzyme in the presence of 3',5'-(d)NDP (step 2). This technology allows the use of lower amounts of RNA ligase to achieve the same coupling rates and efficiencies. The reaction rate enhancement achieved by adding a small amount of 3′,5′-(d)NDP is a function of the RNA ligase concentration. A greater rate enhancement is achieved at lower RNA ligase concentrations.

If unactivated nucleotide substrates, ATP+3′,5′-(d)NDP, are selected for the coupling reaction, it is advantageous to add 3′,5′-(d)NDP at a slight molar excess over ATP for the same reason discussed. When using activated nucleotide substrates, App(d)Np, it is also possible to add pyrophosphate+hexokinase+-glucose to prevent inactivation of RNA ligase. The pyrophosphate regenerates free enzyme from the adenylylated form by the reverse reaction of step 1; hexokinase+glucose hydrolyze the generated ATP to ADP, preventing the ATP from re-adenylylating the enzyme. The ADP is hydrolyzed during Alkaline Phosphatase incubation to adenosine+2(PO₄).

Preactivated blocked nucleotides for use as substrates in the method of the invention can be conveniently synthesized using RNA ligase+3′,5′-(d)NDP+ATP-+Inorganic Pyrophosphatase in the absence of primer and using a slight excess of 3′,5′-(d)NDP. RNA ligase is heat inactivated. Residual ATP is removed by adding hexokinase and glucose; this prevents covalent inactivation of RNA ligase by ATP. Hexokinase is subsequently heat inactivated. The slight excess of 3′,5′-(d)NDP is resistant to hexokinase; trace reaction side products ADP and glucose-6-phosphate do not interfere with the RNA ligase coupling reaction. Activated nucleotides can also be enzymatically synthesized from 3′-(d)NMP and (d)Np(d)Np nucleotides by the addition of phosphatase-free Polynucleotide Kinase. Wild type Polynucleotide Kinase is a bifunctional enzyme with two distinct active sites. One site catalyzes 5′ phosphorylation of nucleotides and oligonucleotides; the other site catalyzes the hydrolysis of 3′- phosphate from nucleotides and oligonucleotides. A mutant version of Polynucleotide Kinase in which the phosphatase function has been selectively eliminated is available commercially from Boehringer Mannheim Biochemicals (Germany), referred to as phosphatase-free Polynucleotide Kinase (PNK). The mechanism for the synthesis of activated nucleotides is summarized below:

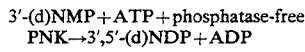
3′-(d)NMP+ATP+phosphatase-free PNK→3′,5′-(d)NDP+ADP

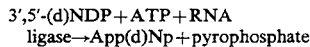
3′,5′-(d)NDP+ATP+RNA ligase→App(d)Np+pyrophosphate

Other substrates which are coupled to the primer by the chain extending enzyme and which can be converted to an inert or slowly reacting product may also be employed.

Blocking Groups

When the blocking group employed on the substrate is a 3′-phosphate group, the enzyme employed in the second step of the method shown in FIG. 2 is a phosphatase.

The principal function of the phosphatase is the irreversible removal of the 3′-phosphate blocking group from the primer (allowing subsequent RNA ligase coupling) and from the nucleotide substrate (preventing subsequent RNA ligase coupling). Two types of Phosphatases are known which are useful for the method of the invention: Non-specific phosphatases such as Alkaline Phosphatase and Acid Phosphatase; and specific 3′-Phosphatases such as Polynucleotide Kinase (PNK).

Alkaline Phosphatase (e.g., from calf intestine, CIAP) is a general phosphatase which degrades nucleotides as follows:

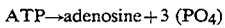
ATP→adenosine+3 (PO₄)

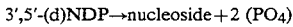
3′,5′-(d)NDP→nucleoside+2 (PO₄)

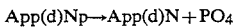
App(d)Np→App(d)N+PO₄

AMP→adenosine+PO₄

CIAP offers the benefit of complete degradation of nucleotides to nucleosides (in the presence of Nucleotide Pyrophosphatase). Nucleosides are substantially non-inhibitory to all the enzymatic reactions of the method. The poor solubility of nucleosides (such as adenosine) at pH 8.0 may result in precipitation out of solution if the concentration accumulates to high levels. Such a precipitation is beneficial in that it removes the nucleoside by-product from solution, making it completely inert to all aspects of the oligonucleotide synthesis, and facilitating separation from the final oligonucleotide product by centrifugation or filtration. CIAP also has inorganic pyrophosphatase activity, not present in PNK, which can hydrolyze pyrophosphate generated by the RNA ligase coupling reaction or pyrophosphate added during RNA ligase coupling to regenerate adenylylated enzyme. The use of dinucleotides, such as App(d)N(d)Np, as substrates for RNA ligase requires the use of Alkaline Phosphatase and a Dinucleotide Pyrophosphate Degrading enzyme, such as Nucleotide Pyrophosphatase for maximum efficiency.

Acid Phosphatase has been isolated from wheat, potato, milk, prostate and semen, and catalyzes the same reactions as Alkaline Phosphatase. Acid Phosphatase can substitute for Alkaline Phosphatase if the pH of the reaction solution is acidic.

PNK is a highly specific 3′-phosphatase which degrades nucleotides as follows:

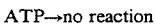
ATP→no reaction

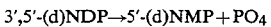
3′,5′-(d)NDP→5′-(d)NMP+PO₄

App(d)Np→App(d)N+PO₄

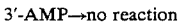
3′-AMP→no reaction

The advantages of PNK are: (1) PNK is useful at the end of an oligonucleotide synthesis to simultaneously phosphorylate the 5′ end (in the presence of ATP) and dephosphorylate the 3′ end, and (2) Phosphoanhydrides are not hydrolyzed, therefore, less PO₄ and acid is generated during the oligonucleotide synthesis. Thus, phosphate concentrations do not accumulate as rapidly.

PNK also has some disadvantages, as follows: (1) The 3′-phosphatase activity for the nucleotide substrates above is substantially slower than Alkaline Phosphatase, requiring longer incubation times or higher enzyme concentrations to achieve the same rate of hydrolysis. (2) AMP which is generated by the RNA ligase coupling reaction is not hydrolyzed and may accumulate after many coupling cycles to levels which inhibit RNA ligase. (3) Cyclization of the oligonucleotide can occur if ATP is employed in RNA ligase coupling reactions. PNK phosphorylates the 5′ hydroxyl in the presence of ATP and dephosphorylates the 3' end of an oligonucleotide. Subsequent RNA ligase addition results in cyclization. Unexpectedly, experimental data strongly suggests that a circular 24-mer oligodeoxyribonucleotide is degraded by both exonuclease I and snake venom phosphodiesterase I. This susceptibility could perhaps be explained by steric strain of the tight ring, exposing binding sites normally hidden in linear oligodeoxyribonucleotides. Thus, while PNK is useful for the method of the invention, the preferred Phosphatase is Alkaline Phosphatase.

Other blocking groups which might be used in the method of the invention include blocking groups which are cleaved by light, in which case the addition of an enzyme to accomplish the unblocking would be unnecessary. Other blocking groups include any chemical group covalently attached to the 2'- or 3'-hydroxyl of App(d)N-3'—OH, which can be removed without disrupting the remainder of the oligonucleotide. This may include esters, sulfate esters, or glucose acetals which can be removed by enzymatic treatment with esterases or peptidases, sulfatases, or glucosidases, respectively.

Blocking groups which can be cleaved by light have been reported in the literature, such as the o-nitro-benzyl group (E. Ohtsuka et al, *Nucleic Acids Research*, (1979), 6(2), 443–54). This innovation is in concert with the One Pot enzymatic method, since it does not require intermediate purification of the synthesized oligonucleotide. Thus, light can be used in the invention in place of an enzyme for removing the blocking group from the end of the oligonucleotide and from any unreacted substrate molecules.

Additional Method Steps and Materials

To synthesize longer oligonucleotide sequences, it is desirable to overcome two potential problems: the extension of the chain with unreacted nucleotide of the wrong type, and the subsequent extension of failed reaction products (unextended primer) from a previous cycle. These problems can be overcome by the addition of one or more additional enzymes to the basic scheme shown in FIG. 2.

To minimize the incorporation of residual nucleotides from previous reaction cycles, an additional enzyme can be added during or prior to the unblocking step which is effective to degrade residual substrate into products that are no longer suitable substrates for RNA ligase, and that do not inhibit RNA ligase or Alkaline Phosphatase at high concentrations.

A suitable enzyme for this purpose is a Dinucleotide Pyrophosphate Degrading Enzyme. Five distinct enzymes are capable of degrading App(d)N and App(d)Np, as described in the scientific literature:

(1) Nucleotide Pyrophosphatase (E.C. 3.6.1.9):

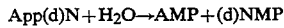

(2) Acid Pyrophosphatase (Tobacco, Sigma Chemical Co.):

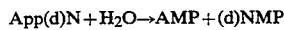

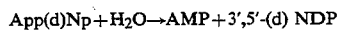

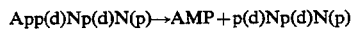

(3) Diphosphopyridine Nucleosidase or DPNase (E.C. 3.2.2.5):

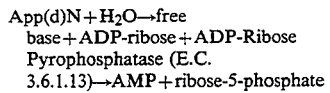

(4) Dinucleotide Pyrophosphate Deaminase (Kaplan et al, *Journal of Biological Chemistry*, (1952), 194, 579–91):

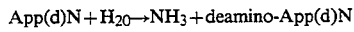

(5) Dinucleotide Pyrophosphate Pyrophosphorylase (A. Kornberg, (1950), *Journal of Biological Chemistry*, 182, 779–93):

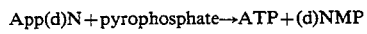

These enzymes are suitable for this invention because the degradation products are not substrates for RNA ligase. Among the Dinucleotide Pyrophosphate Degrading Enzymes, the preferred enzyme is Nucleotide Pyrophosphatase. This enzyme offers the following advantages: the reaction is irreversible, the enzyme degrades both App(d)N and App(d)Np, such that unblocking with phosphatase does not have to be done previously; the dinucleotides are hydrolyzed to nucleosides+$PO_4$ when used with Alkaline Phosphatase, and the enzymatic properties have been thoroughly studied.

Of these enzymes, DPNase and tobacco acid phosphatase are commercially available (Sigma Chemical Co, St. Louis, Mo.). Nucleotide Pyrophosphatase has been isolated from a great number of sources: human fibroblasts, plasmacytomas, human placenta, seminal fluid, Haemophilus influenzae, yeast, mung bean, rat liver, and potato tubers. The source with the best characterized enzymatic properties is potato tubers (M. Bartkiewicz et al, *Eur. J. Biochem.*, (1984), 143, 419–26). Bartkiewicz et al have shown that purified enzyme is capable of hydrolyzing dinucleotide pyrophosphates specifically, without hydrolyzing DNA or RNA.

Sigma Chemical Company (St. Louis, MO) sells an enzyme preparation advertised as Nucleotide Pyrophosphatase isolated from snake venom. However, no reports exist in the scientific literature of the existence of Nucleotide Pyrophosphatase in snake venom. Experiments have confirmed that the enzyme responsible for Nucleotide Pyrophosphatase activity in the snake venom is, in fact, the enzyme Phosphodiesterase I (PDE-I); that is, PDE-I from snake venom also hydrolyzes dinucleotide pyrophosphates. Accordingly, PDE-I can also be used to convert unreacted nucleotides into a form which does not serve as a substrate for RNA ligase.

The second potential difficulty with the method of the invention arises from a build up of failure sequences due to incomplete RNA ligase coupling. The RNA ligase coupling reaction can be substantially optimized kinetically in accordance with the invention. Dithiothreitol and TRITON X-100 (octylphenoxy polyethoxy ethanol) greatly stimulate RNA ligase activity. Nevertheless, even under optimized conditions, the coupling reaction is not 100% efficient, resulting in primer chains which have not been coupled to the blocked nucleotide. If not removed, these unreacted primer chains will still be able to couple with nucleotide in the next coupling cycle. This will result in the accumulation of (n−1) failure sequences in the final product mix. The accumulation of these failure sequences will necessitate a difficult purification of the desired oligonucleotide product at the end of the synthesis. Two independent solutions have been devised to solve this problem: Exonuclease treatment and Enzymatic Capping.

Exonuclease can be added after RNA ligase coupling to completely hydrolyze uncoupled primer chains to (d)NMP's. The Exonuclease can be utilized before, after, or concurrently with the dinucleotide cleaving enzyme, and is subsequently inactivated by heat prior to incubation with Phosphatase. The Exonuclease used for this purpose should have the following properties:

(1) hydrolyzes oligonucleotides in the 3' to 5' direction.
(2) hydrolyzes specifically oligonucleotides with a free terminal 3' hydroxyl group and is substantially unable to hydrolyze oligonucleotides which are blocked at the 3' end
(3) hydrolyzes oligoribonucleotides or oligodeoxyribonucleotides or both.

Primer chains which fail to couple during incubation with RNA ligase differ from primer chains which do couple. Uncoupled primers have a 3'-hydroxyl terminus; coupled primers have a blocked 3'-phosphate. Therefore, as a result of the selectivity of the Exonuclease, only uncoupled primer chains will be degraded to (d)NMP's. Exonuclease incubation should be performed prior to incubation with Phosphatase. Exonuclease must be inactivated prior to Phosphatase addition; otherwise, oligonucleotide product will be hydrolyzed.

Three enzymes satisfy these criteria and are suitable as Exonuclease in this invention: Exonuclease I (*E. coli*), Phosphodiesterase I (snake venom), and Polynucleotide Phosphorylase+$PO_4$. Phosphodiesterase I hydrolyzes both oligoribonucleotides and oligodeoxyribonucleotides; Exonuclease I is substantially specific for oligodeoxyribonucleotides (although it has been used successfully on mixed deoxyribose/ribose oligonucleotides); Polynucleotide Phosphorylase is substantially specific for oligoribonucleotides. Polynucleotide Phosphorylase suffers from a disadvantage in that since the reaction is reversible, a substantial excess of $PO_4$ should be present to ensure complete phosphorolysis. TRITON X-100 and dithiothreitol have been observed experimentally to stimulate the activity of Exonuclease I and Phosphodiesterase I.

Phosphodiesterase I (PDE-I) offers two advantages: (1) PDE-I hydrolyzes oligoribonucleotides and oligodeoxyribonucleotides, making it useful for the synthesis of both, and (2) PDE-I also catalyzes the hydrolysis of dinucleotide pyrophosphates, such as App(d)N or App(d)Np, to their respective mononucleotides. One possible disadvantage encountered with snake venom PDE-I is that if enzymatic conditions are not carefully controlled, primer chains blocked by a 3'-phosphate will also be degraded. That is, PDE-I has a lower specificity than Exonuclease I or Polynucleotide Phosphorylase. Fortunately, enzymatic conditions can be achieved such that substantially all 3'-hydroxyl primer chains are hydrolyzed without hydrolyzing 3'-phosphate primer chains. Given that it is advantageous to use Dinucleotide Pyrophosphate Degrading activity and Exonuclease activity, snake venom PDE-I provides two functions for the price of one enzyme. The mononucleotide products are subsequently degraded by Alkaline Phosphatase to $PO_4$ and nucleosides.

Figure 3:
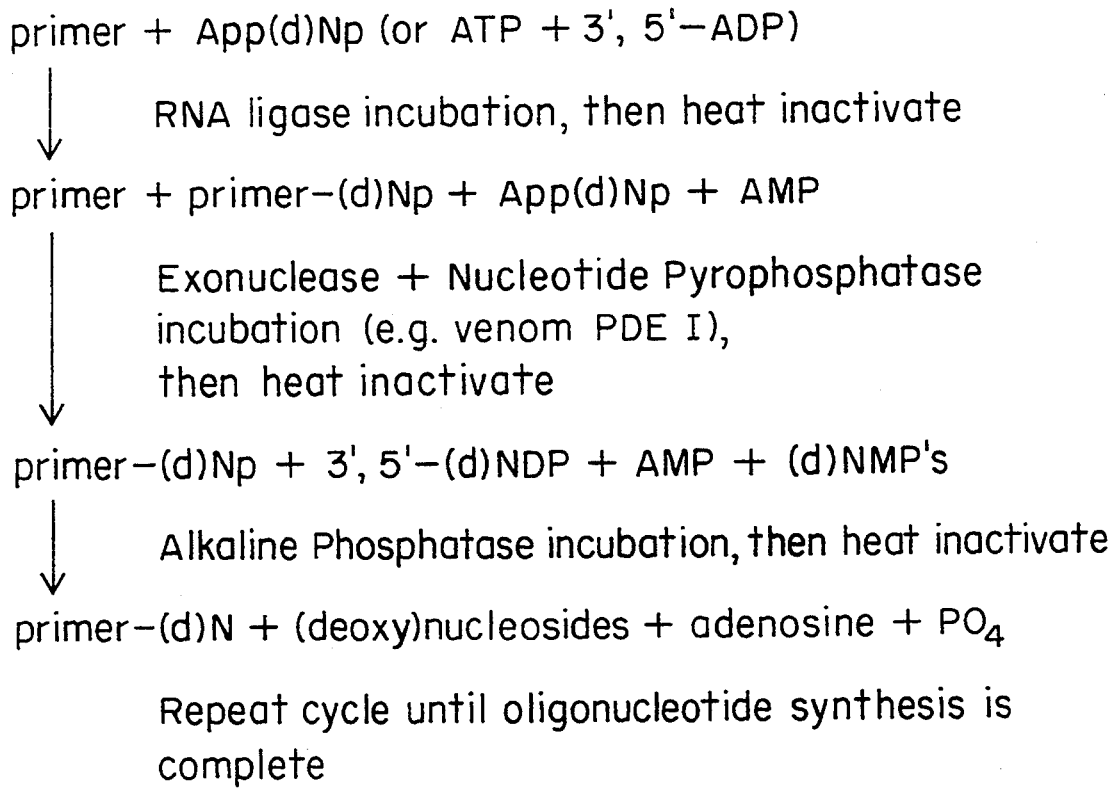
FIG. 3: The Preferred One Pot enzymatic method for the synthesis of oligonucleotides. The preferred method eliminates all failure sequences by removing unreacted primer chains with Exonuclease and degrading dinucleotide pyrophosphate with Nucleotide Pyrophosphatase. Snake Venom Phosphodiesterase I contains both of these enzymatic activities.

The combination of these two modifications to the basic method result in the Preferred method for the synthesis of oligonucleotides, outlined in FIG. 3. The power of this method is exemplified in Example 5. ApApCpdApdA is synthesized by two coupling cycles with the activated nucleotide AppdAp and an ApApCp initial primer. Thin layer chromatography demonstrated that the reaction mixture at the end of the synthesis contained only oligonucleotide product ApApCpdApdA and the nucleosides adenosine and deoxyadenosine. The mixture was devoid of traces of n−1 and n−2 failure sequences. Due to the enormous size difference between the n-mer oligonucleotide product and the nucleosides, the oligonucleotide product can be easily purified. Furthermore, an application may not require removal of the nucleosides.

As mentioned earlier, another technique can be used to remove uncoupled primer chains—Enzymatic Capping. After the RNA ligase coupling reaction, unreacted primer chains can be capped with a chain terminating nucleotide catalyzed by a transferase enzyme. The capped chains are no longer substrates for coupling with RNA ligase in subsequent coupling cycles. Primer chain termination can be achieved with Terminal deoxynucleotidyl Transferase (TdT)+dideoxynucleoside triphosphate (ddNTP) or with RNA ligase+AppddN (the dideoxy analog of AppdN). The ability of TdT to incorporate ddNTP is well established in the scientific literature. Furthermore, the activity of TdT is markedly increased in the presence of 0.1% TRITON X-100. Using this technique, failure sequences will be capped with a chain terminating nucleotide. Chain terminated failure sequences can be selectively hydrolyzed as follows. Prior to removal of the 3'-phosphate blocking group using phosphatase, Exonuclease is added to specifically degrade all primer chains with a free 3'—OH or 3'-chain terminated end. Oligonucleotide product is not degraded by Exonuclease because it is blocked by a 3'-phosphate. Exonuclease is subsequently heat inactivated, and the cycle is continued with Alkaline Phosphatase catalyzed removal of the 3'-phosphate blocking group. The Exonuclease incubation is preferably done once at the end of the oligonucleotide synthesis. Exonuclease used with this technique should have the same properties as the Exonuclease above, with the additional requirement that the Exonuclease is capable of hydrolyzing primer chains terminating in a dideoxynucleoside. Experiments have confirmed that Exonuclease I (*E. coli*) and Phosphodiesterase I (snake venom) fulfill these criteria. It is expected that Polynucleotide Phosphorylase will also be suitable.

Like the Exonuclease method described above, the final products of the oligonucleotide synthesis are the oligonucleotide product and nucleosides. One potential drawback of the enzymatic capping technique for removing uncoupled primer chains is the coupling efficiency of the chain terminating step. If the coupling efficiency is low, then (n−1) failure sequences will be present in the final solution mixture. It has also been observed experimentally that Terminal deoxynucleotidyl Transferase (TdT) is stable at 95° C. for 5 minutes in the presence of 0.1% TRITON X-100. This would then necessitate inactivation of TdT with proteinase K, followed by heat inactivation of proteinase K. Thus, although the Enzymatic Capping technique is effective, the favored method for removing uncoupled primer chains is the Exonuclease method discussed earlier.

The method of the invention can be supplemented with additional enzymes which help to drive the thermodynamics of the RNA ligase reaction. The first step of the RNA ligase reaction mechanism, adenylylation by ATP, is reversible. Supplementation with Inorganic Pyrophosphatase drives this step to completion by irreversibly hydrolyzing pyrophosphate to phosphate. Inorganic Pyrophosphatase is therefore especially useful if unactivated nucleotide substrates are selected for RNA ligase coupling; Inorganic Pyrophosphatase can also be used with activated nucleotide substrates to remove residual pyrophosphate, preventing an undesirable build up of pyrophosphate which may be a contaminant of enzyme or nucleotide preparations Hydrolysis of pyrophosphate by Inorganic Pyrophosphatase prevents precipitation of magnesium pyrophosphate, which is highly insoluble in aqueous solutions.

Another useful enzyme for optional supplementation of the method is 5'-Nucleotidase. This enzyme can be added during RNA ligase coupling to help drive the coupling step of the reaction to completion by irreversibly hydrolyzing AMP to adenosine+$PO_4$. 5'-Nucleotidase can be used with either unactivated or activated nucleotide substrates, since 5'-Nucleotidase cannot hydrolyze 3',5'-(d)NDP. Reactions catalyzed by these enzymes are summarized below: pyrophosphate+$H_2O$+Inorganic Pyrophosphatase→2($PO_4$) AMP+$H_2O$+5'-Nucleotidase→Adenosine+$PO_4$ The enzyme Nucleoside Phosphorylase (E.C. 2.4.2.1), which hydrolyzes nucleosides to free bases+ribose-1-phosphate, can be added during Phosphatase incubation. Free bases, such as adenine, are poorly soluble in aqueous solution at pH 8.0, which may result in a beneficial precipitation from solution. The other product, ribose-1-phosphate, is subsequently degraded to ribose+$PO_4$ by CIAP.

In practicing the method of the invention, inactivation of the various enzymes can be readily accomplished using heat. It may also be desirable to add a protease, e.g., proteinase K. Protease can be subsequently inactivated by heat.

Proteolysis with proteinase K serves a dual role. Not only does this protease inactivate any enzyme in the solution, it also hydrolyzes the denatured protein debris which accumulates during the synthesis of an oligonucleotide. This denatured protein debris is generated by heat inactivation of the enzymes. This debris is inert; it is not in solution and does not bind or inhibit any of the components in the synthesis reactions. Unfortunately, this debris may accumulate after many cycles to such an extent that it may pose a clogging hazard for pipetting operations. Proteinase K will hydrolyze the debris to small soluble peptides, removing this hazard. The proteinase K can be subsequently inactivated by heat or by chemical inhibitor such as phenymethylsulfonyl chloride. The proteolytic digestion may be enhanced by the addition of TRITON X-100.

Physical methods for removing the debris can also be utilized, such as filtration, ultrafiltration, centrifugation, and extraction with organic solvents such as phenol and chloroform. Since these physical methods entail manual intervention, they would be more appropriate if performed after the completion of the oligonucleotide synthesis. The use of protease to solve this problem is in concert with the "one pot" concept, since no manual intervention is required. Proteinase K can also be used to inactivate any enzyme in the reaction solution, such as enzymes used to cleave the oligonucleotide, to digest the initial primer, or to make a complementary oligodeoxyribonucleotide.

The method of the invention is particularly well adapted to the synthesis of oligoribonucleotides. It can also be used to synthesize oligodeoxyribonucleotides, although coupling times will be longer and coupling efficiencies will be lower.

For most applications an oligoribonucleotide can be substituted for an oligodeoxyribonucleotide with equal effectiveness. Oligoribonucleotides have been used as hybridization probes, and should also be useful as primers for DNA sequencing and as primers for the polymerase chain reaction and the ligase chain reaction. Oligoribonucleotides can be readily cloned into plasmids in a manner similar to oligodeoxyribonucleotides using DNA ligase. (U.S. No. Pat 4,661,450). This technology opens the use of oligoribonucleotides for widespread general recombinant DNA applications, such as site-directed mutagenesis, antisense probes, and synthetic gene construction.

Figure 5:
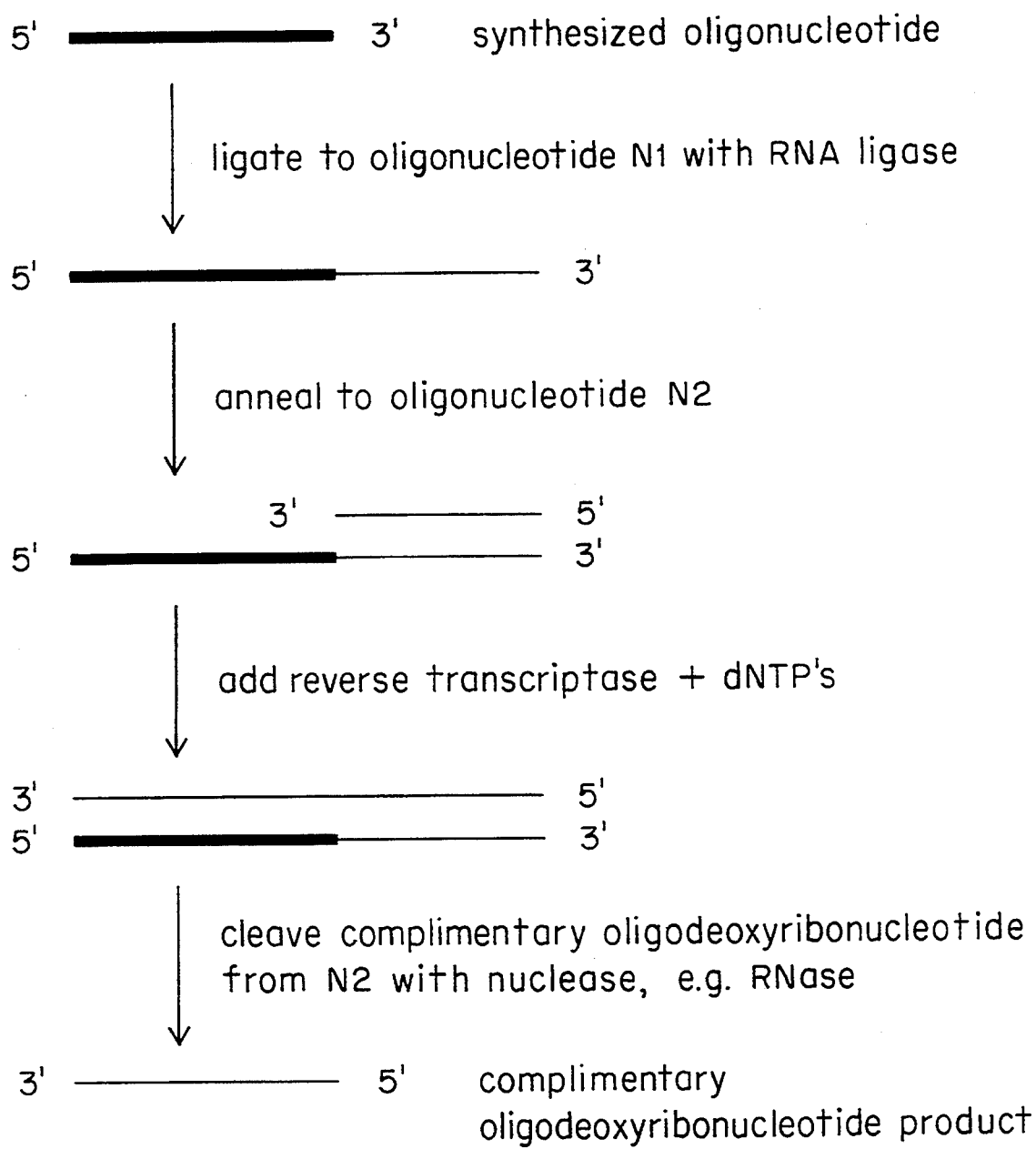
FIG. 5: Outline of method for converting synthesized oligonucleotide to complementary oligodeoxyribonucleotide.

For applications which have an absolute requirement for oligodeoxyribonucleotides, one approach is to initially synthesize a complementary oligoribonucleotide, then to subsequently convert it to its complementary oligodeoxyribonucleotide. This approach can be implemented in a "one pot" manner and is outlined in FIG. 5. An oligonucleotide (N1) is ligated to the 3' terminus of the synthesized oligoribonucleotide with RNA ligase. Another oligonucleotide (N2) is added which anneals to N1. Reverse transcriptase+dNTP's are added to copy the synthesized oligoribonucleotide to a single stranded DNA copy. The use of excess N2, a thermostable reverse transcriptase, and thermal cycling will allow linear amplification of the number of single stranded DNA copies. A nuclease is added to liberate the single stranded DNA from the RNA. The result is an oligodeoxyribonucleotide which is complementary to the synthesized oligoribonucleotide. This method is preferably performed in which N1 and N2 are oligoribonucleotides and RNase is used to liberate the complementary oligodeoxyribonucleotide.

The method of the invention is particularly well suited for the simultaneous production of many oligonucleotides in individual vessels. In this embodiment, quantities of oligonucleotide of about 50 ug are readily synthesized in a volume of 100 ul. These quantities are sufficient for most purposes. In some cases, larger quantities of oligonucleotide product may be needed, in which case concerns about the cost of the enzymes used may militate in favor of enzyme recovery techniques rather than enzyme destruction or an enzyme column approach as illustrated in FIG. 6. For example, in the past few years the need for bulk quantities of oligonucleotides has been established especially for use as antisense oligonucleotides as a potential therapy for diseases such as cancer, HIV, hepatitis, etc.

In the Enzyme Recovery technique, instead of inactivating the enzymes by heat or proteolytic treatment, the enzymes are mainly "inactivated" by passing the reaction solution through an affinity column which binds to the enzyme; other components of the reaction solution, such as oligonucleotide and nucleosides, will pass through the column freely. Residual enzyme activity present in the reaction solution can be subsequently inactivated by heat or proteolytic treatment. The recovered enzyme, bound to the column, can be eluted and reused for subsequent cycles.

This modification is favorably implemented by manufacturing the enzymes as fusion proteins. Fusion proteins are proteins in which the functional enzyme of interest (e.g. RNA ligase, phosphodiesterase I or alkaline phosphatase) is covalently bound to an affinity peptide by fusing the genes for the enzyme and the affinity peptide in an expression vector. Because of the high specific binding affinity of the affinity peptide for an affinity support, the fusion protein can be purified to near homogeneity in one step using affinity chromatography.

The genes coding for T4 RNA ligase and Alkaline Phosphatase have been sequenced and cloned. (Rand et al., *EMBO Journal* 3, 397–402 (1984) and M. Lowe et al, *Biochim. Biophys. Acta,* 1037, 170–7, (1990).) Thus, these enzymes could be readily converted into a fusion protein, e.g. using one of the several commercially available fusion protein systems: Glutathione-S-Transferase (Pharmacia-LKB), Maltose Binding Protein (New England Biolabs), Cellulose Binding Protein, Xpress metal ion affinity (Qiagen) and Avidin (Pharmacia-LKB).

The affinity matrix used for the manufacture of the fusion protein can be used in accordance with the invention to recover enzyme. The enzyme may require an additional purification step prior to reuse, in order to remove trace quantities of oligonucleotides and nucleotide substrates or to remove the chemical used to elute the enzyme from the affinity matrix (e.g. NaCl or glutathione for the Glutathione-S-Transferase fusion system). This recovery approach is made practical as a result of the experimental observation that all the enzymes used in the Preferred One Pot method are highly stable at 37° C. in the presence of TRITON X-100; thus, the enzymes will still be highly active after an incubation step. This recovery approach has the added benefit of reducing the amount of insoluble protein debris generated by heat inactivation of the enzymes. To illustrate cost savings, if the average enzyme recovery rate is 90% after each cycle, then the required amount of enzyme to synthesize a typical 15-mer will be reduced ten-fold.

An alternative approach to reusing enzymes is shown in FIG. 6. In the Enzyme Column technique, the enzymes are covalently attached to a solid support bead, such as silica, dextran, or sepharose. Covalent attachment of enzymes is accomplished by incubating the enzymes with an activated form of the solid support. Aldehyde, cyanogen bromide, tresyl and epoxide activated supports are commercially available from various sources, e.g., Sigma Chemical Co., Pharmacia, and Sterogene, Inc. Enzymes are usually bonded to the support at several locations through available amino or thiol groups.

The enzymes are added to the reaction solution as beads. After the enzyme incubation step, the enzyme is "inactivated" by simply removing the solid beads, e.g. filtration. The enzyme-beads can be washed for reuse in subsequent cycles. This approach is feasible since covalent attachment of enzymes to solid supports does not substantially affect the enzyme activity. In fact, covalent attachment usually increases an enzyme's stability. Continuous mixing of the reaction solution would ensure that substantially all solution diffuses to the solid bead.

A more practical mode for using enzymes covalently attached to solid supports is to construct columns containing the enzyme-bead and in which reaction solution is pumped through a column containing the enzyme covalently attached to the solid support. Recirculation can be used if an extended incubation period is needed. The placement of enzyme-solid support in columns would facilitate automation, since enzyme-beads could be regenerated by simply washing the column with wash buffer. Furthermore, a support can consist of a mixture of two or more enzymes. For example, a mixture of RNA Ligase and 5'-Nucleotidase can be covalently attached to sepharose for use in the coupling reaction. A system of valves would direct the flow of the reaction solution into the appropriate enzyme column. Leakage of the enzymes from the solid support may entail a heat or proteolytic inactivation step to remove residual enzyme activity in the solution; whether this step is necessary is dependent on the leakage rate of the solid support.

For the method of the invention to work in an effective manner, it is important that inhibition of the various enzymes, and particularly RNA ligase, by the by-products of the reactions be minimal. To confirm that this is the case, experiments were performed on each of the reaction by-products with the result that no significant inhibition was found.

The major by-products of the method of the invention are nucleosides and $PO_4$. No inhibition was detected in the presence of 10 mM $PO_4$ and 10 mM Adenosine (a typical nucleoside). Extremely weak inhibition was observed in the presence of 100 mM $PO_4$. In addition, other nucleotides were tested for inhibition: no inhibition was detected in the presence of 10 mM Adenine, 1 mM AMP, 1 mM ATP, 2 mM AppA and 10 mM 3',5'-ADP; extremely weak inhibition was detected in the presence of 10 mM Pyrophosphate; and strong inhibition was observed in the presence of 10 mM AMP and 10 mM ATP. Therefore, the only two products which are strong inhibitors, ATP and AMP, and one product which is an extremely weak inhibitor, Pyrophosphate, will never accumulate to these high concentrations since they are degraded after each cycle by Alkaline Phosphatase (ATP, AMP, and Pyrophosphate), 5'Nucleotidase (AMP), or Inorganic Pyrophosphatase (Pyrophosphate). Phosphate will accumulate to 100 mM concentration only after approximately 40 synthetic cycles, and only trivial enzymatic inhibition is observed at this concentration.

The hydrolysis of phosphate anhydrides by Alkaline Phosphatase and Nucleotide Pyrophosphatase, and the hydrolysis of phosphodiesters by Exonuclease releases an equivalent of acid ($H_2PO_4^- \rightarrow HPO_4^{-2} + H+$), which may result in an undesirable drop in the pH of the reaction solution. Solution pH should be maintained within a suitable range to ensure the optimal activity of the enzymes. Thus, the synthesis of long oligonucleotides may necessitate the occasional addition of base (such as NaOH or Tris) to prevent an undesirable drop in the solution pH.

Alternatively, a high concentration of buffer can be used such that the anticipated acid generation will not significantly alter the pH. For example, if 1 mM App(d)Np substrate is added in each cycle of the Preferred One Pot method, each cycle will generate 1 mM acid. The synthesis of a 15-mer will not generate enough acid to significantly change the pH if the buffer is 150 mM Tris-Cl. The synthesis of a 50-mer will generate 50 mM acid; this may cause the pH to drop below an acceptable range. This can be solved by adding 10 mM base after every 10 coupling cycles, to neutralize the generated acid.

A potential problem also exists with the accumulation of $PO_4$. Phosphate concentrations exceeding about 20 mM at pH 8.0 and 10 mM $MgCl_2$ may eventually precipitate the magnesium as $MgPO_4$. This is deleterious since magnesium is a required cofactor for many of the enzymes in the One Pot method. This problem can be solved by using a lower reaction solution pH of 7.0; a buffer such as BES (N,N-bis-[2-hydroxyethyl]-2-aminoethanesulfonic acid, Sigma Chemical Co.) is more suitable than Tris for pH 7.0. Experiments confirm that no precipitation of $MgPO_4$ is observed in a solution of 10 mM $MgCl_2$ and 250 mM $PO_4$ at pH 7.0.

While the foregoing describes the basic aspects of the claimed invention, it will be appreciated that numerous modifications are possible without departing from the basic invention. For example, a potential problem is growth in the reaction mixture of microorganisms. These microorganisms may secrete nucleases which could degrade the nucleotides and oligonucleotides. This problem is mitigated by the frequent heat inactivation steps which effectively sterilize the reaction solution and the use of the detergent TRITON X-100 in the reaction solution which kills most microbes. TRITON X-100 has the added benefit of stimulating the activity and increasing the stability of the preferred enzymes used in the invention. However, long incubation periods may be necessary for difficult coupling reactions, for example, in the synthesis of oligodeoxyribonucleotides using RNA ligase. These microbes may be present in non-sterile reagents which are added to the reaction solution during each cycle. These situations foster microbial growth. A simple solution is the addition of microbial growth inhibitors, such as glycerol, EDTA, sodium azide, merthiolate, or antibiotics. Glycerol acts as a preservative at concentrations of about 5% to 50%. Glycerol has the added benefit of stabilizing the enzymes used in the synthesis. EDTA should be used at concentrations lower than the $Mg^{+2}$ concentration; it inhibits microbial growth by strongly binding to divalent cations which are needed for microbial growth. EDTA has the added benefit of chelating cations which may contaminate the solution and which may also inhibit the enzymatic reactions such as $Ca^{+2}$, $Fe^{+2}$, and $Zn^{+2}$. A useful growth inhibitor for the method of the invention must not significantly inhibit the enzymatic reactions in the synthesis of the oligonucleotide. This criterion was met by 0.1% sodium azide and 0.1% merthiolate, with no significant inhibition of RNA ligase observed.

If nuclease contamination of the synthesis reaction is a problem, nuclease inhibitors can be added at a concentration sufficient to block their degradation of the oligonucleotide, while not significantly inhibiting the synthetic enzymatic reactions. This precautionary measure may be especially important for RNase contamination, since most RNases are stable to heating at 95° C. (but not stable to proteolysis). Examples of nuclease inhibitors include RNase Inhibitor (human placenta, Sigma Chemical Co.) and Vanadyl Ribonucleoside Complexes (Sigma Chemical Co). Since RNase Inhibitor is inactivated by heat or proteolysis, it would need to be replenished after an inactivation step. Vanadyl ribonucleoside complexes are stable to both heat and proteolysis, probably would not require replenishment, and are readily removed from aqueous solution by extraction with phenol: chloroform: 8-hydroxyquinolone. No significant inhibition of RNA ligase is observed in the presence of 0.1 mM vanadyl ribonucleotide complexes.

Evaporation may present a problem during oligonucleotide synthesis. This problem can be minimized by reducing the temperature or duration of the heat inactivation step or by overlaying the aqueous phase with light mineral oil. For example, snake venom PDE-I can be inactivated by heating at 50° C. for 5 minutes; commercially available heat labile alkaline phosphatase from Arctic fish can be inactivated at 65° C.

Dithiothreitol, or other reducing agents, stimulate the activity of the enzymes used in the One Pot method, especially RNA ligase. The long duration of an oligonucleotide synthesis may result in the consumption of DTT by oxidation; thus, it may be necessary to intermittently add DTT to the solution to replenish the DTT lost to oxidation.

In some cases, the formation of secondary structure in the product oligonucleotide can give rise to difficulties, e.g., if the oligonucleotide can form loop structures by annealing to itself which block enzymatic access to the 3'-end of the oligonucleotide. To prevent this, the oligonucleotide can be synthesized as several smaller pieces which do not self anneal and then ligated together, e.g. with RNA ligase. Alternatively, the base portion of the nucleotide can be reversibly modified with protecting groups such as acetyl groups which prevent them from base pairing. The protecting groups are removed at the end of the synthesis.

A third alternative for avoiding problems caused by formation of secondary structure is the addition of denaturants to the reaction mixture which disrupt oligonucleotide base pairing without substantially inhibiting the enzymatic reactions. Suitable denaturants include dimethyl sulfoxide, formamide, methylmercuric hydroxide and glyoxal. No significant inhibition of RNA ligase was observed in the presence of 20% dimethyl sulfoxide.

Construction of an RNA ligase mutant form which catalyzes only the third step of the reaction mechanism and does not catalyze the first two steps, has been suggested although not actually produced (S. Heaphy et al., *Biochemistry*, (1987), 26, 1688-96). Such a mutant enzyme would not be subject to inactivation by adenylylation, and it should catalyze the coupling step at a faster rate. Similarly, Terminal deoxynucleotidyl Transferase, Polynucleotide Phosphorylase, and Ribozyme Nucleotidyl Transferase (U.S. Pat. No. 4,987,071) are all incapable of polymerizing their corresponding 3'-phosphate nucleotide analogs. A suggestion has been made in the literature for producing a mutant form of TdT capable of coupling dNTP-3'-phosphate. (L. M. S. Chang et al, CRC Critical Reviews in *Biochemistry*, vol. 21(1), 27–52). Mutant forms of TdT, PNP and Ribozyme Nucleotidyl Transferase which could couple their respective 3'-phosphate analogs would also be useful. The method of the invention is applicable for such future enzymes without modification.

Apparatus

Figure 7:
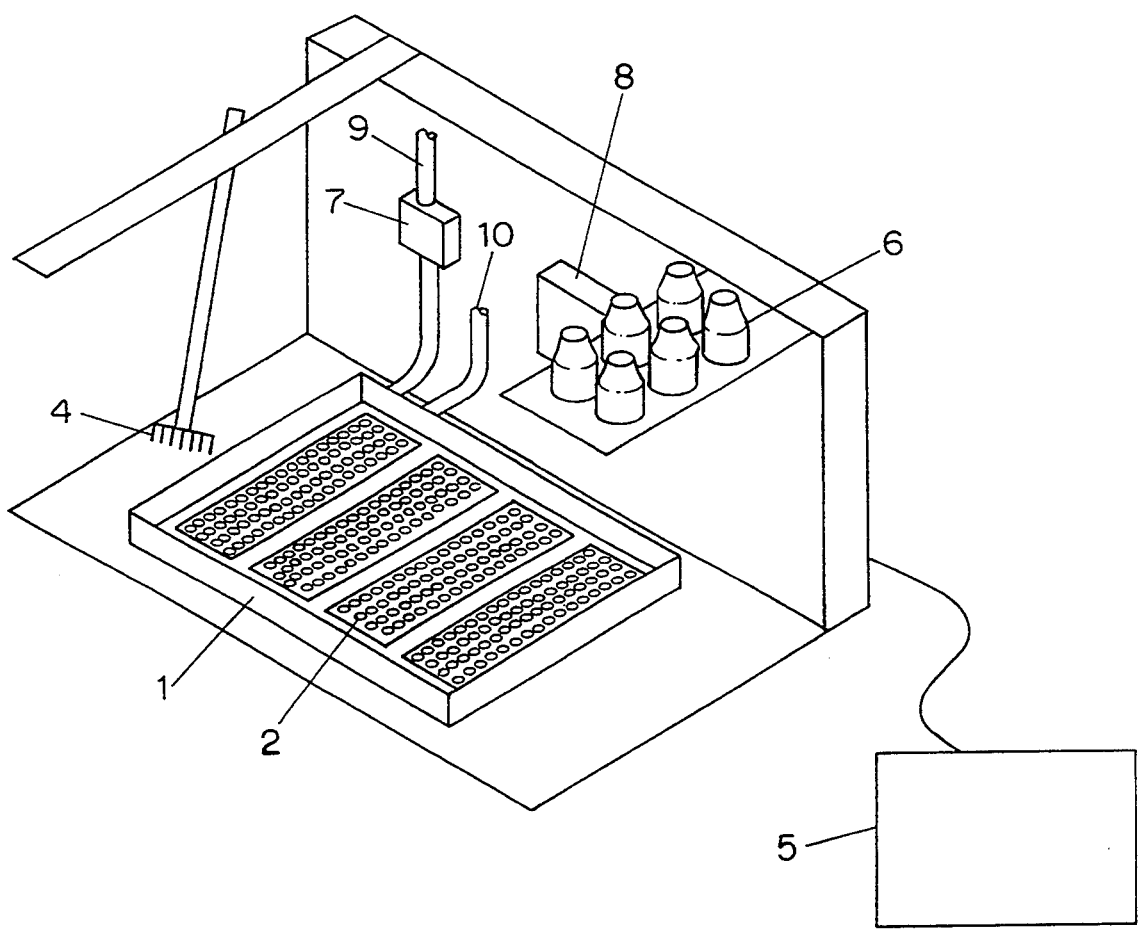
FIG. 7: Automated instrument for the synthesis of oligonucleotides using the One Pot enzymatic method.

FIG. 7 shows an apparatus which can be used in the practice of the invention. The apparatus has a plurality of reaction vessels in the form of wells 2 drilled in a metal block 1. At least four different blocked nucleotide feed stocks and a chain extending enzyme are provided from reagent bottles 6 using liquid handling robot 4. A computer 5 controls the sequential addition of blocked nucleotides and chain extending enzyme to the vessels.

The temperature of the block 1 can be controlled using a heating element or using a circulating water temperature control system comprised of a valve 7, a water inlet 9, a cooling cavity (not shown) and a water exit 10. The computer 5 can control the temperature to provide suitable temperatures for the enzymes reactions, or to raise the temperature if heat is being used for enzyme inactivation.

In an alternative apparatus, the enzymes used for synthesizing oligonucleotides are immobilized on columns. Thus, as shown in FIG. 8A, an apparatus according to the invention comprises a first column 81 containing RNA ligase and optionally 5'-nucleotidase bound to a solid support; and a second column 82 containing a phosphatase enzyme bound to a solid support. Reaction mixture containing primer and the blocked oligonucleotide to be added to the primer is introduced into the top 83 of the first column 81. The reaction mixture flows through the first column 81 (with recirculation in the first column if necessary) and then through the second column 82 (with recirculating if necessary). The reaction mixture is collected from the bottom of the second column 82 and recycled via line 84 to the top 83 of first column 81 where it is reintroduced into the first column 81 together with a reagent stream containing the next blocked nucleotide to be added.

The temperature of the reaction mixture in and between the first and second columns is controlled separately. For example, the first and second column will advantageously have temperature control jackets 85 and 85' which will maintain the temperature within the columns at a suitable temperature for the enzyme reaction. If heat is used to inactivate any enzyme leakage from the columns, separate heating elements 86 and 86" may be used after the first or second columns.

The apparatus may also include a third column 87 as shown in FIG. 8B. The third column 87, which is disposed between the first and the second column, contains an exonuclease and a nucleotide pyrophosphatase immobilized on a solid support. Temperature within the third column 87 is controlled by temperature jacket 85". An additional heating element 86" may be disposed after the third column to inactivate enzymatic leakage.

Reagents

Several of the reagents useful in the practice of the invention have not been previously described, and these reagents are an aspect of the present invention. In particular, the activated deoxyribonucleotides AppdAp, AppdGp and AppdCp; phosphorothioate derivatives of App(d)Gp; AppUp, App(d)Cp, AppdAp and AppdTp; and dinucleotides of the general formula App(d)N$_1$p(d)N$_2$p, wherein N$_1$ and N$_2$ are any nucleosides.

The activated deoxyribonucleotides and the phosphorothioate derivatives can be synthesized by phosphorylation of the 5'-hydroxy of the corresponding 3'-(d)NMP using phosphatase free polynucleotide kinase and ATP or (gamma-thio)-ATP, to yield 3',5'-(d)NDP. This is then activated using RNA Ligase and Inorganic Pyrophosphatase and ATP as described in Example 1.

The dinucleotides can be synthesized in several steps. First, (d)N$_1$p(d)N$_2$p(d)N$_3$ is synthesized chemically, for example using the phosphoramidite method. This product is then phosphorylated using ATP and Polynucleotide Kinase to yield p(d)N$_1$p(d)N$_2$p(d)N$_3$. The enzyme is then inactivated.

The phosphorylated material is then partially digested, e.g. using RNase, DNase or a nuclease to yield p(d)N$_1$p(d)N$_2$p. The enzyme activity is then removed using protease followed by heat, after which the material is activated as in example 1.

The method will now be further described by way of the following, non-limiting examples.

EXAMPLE 1

Enzymatic Synthesis of AppAp and AppdAp

The synthesis of activated nucleotides, App(d)Np and App(d)Np(d)Np can be performed enzymatically using RNA ligase + Inorganic Pyrophosphatase. This example demonstrates the synthesis of AppAp and AppdAp; other activated nucleotides can be synthesized in the same manner.

The following solution in a total volume of 300 ul was placed in an ependorf tube: 50 mM Tris-Cl, pH 8.0, 10 mM MgCl$_2$, 10 mM Dithiothreitol (DTT), 0.1% TRITON X-100, 11 mM 3',5'-ADP, 10 mM ATP, 0.1 units Inorganic Pyrophosphatase (yeast, Sigma Chemical Co.), 80 units RNA ligase (phage T4, New England Biolabs). For the synthesis of AppdAp, 3',5'-dADP was used in place of 3',5'-ADP. This solution was incubated at 37° C. for 40 hours. RNA ligase was heat inactivated at 95° C. for 5 minutes. Residual ATP was removed by adding 2 units Hexokinase (yeast, Sigma Chemical Co.)+15 ul 200 mM glucose and incubating at 37° C. for 1 hour. Hexokinase was heat inactivated at 95° C. for 5 minutes. The solution was cooled to room temperature and pelleted at 12,000 g for 1 minute to remove the insoluble protein debris. This final product was analyzed by thin layer chromatography (TLC) on silica using isobutyric acid:concentrated ammonium hydroxide:water at 66:1:33 containing 0.04% EDTA. No ATP was detected; the major product was App(d)Ap with a small amount of 3',5'-ADP present. AppAp and AppdAp prepared in this manner was used in all the following examples.

EXAMPLE 2

One Pot Synthesis of ApApCpApA

The following solution was placed in a total volume of 40 ul in an ependorf tube: 50 mM Tris-Cl, pH 8.0, 10 mM MgCl$_2$, 10 mM DTT, 0.1% TRITON X-100, 1 mM ApApC primer, 5 mM AppAp. The following procedures were performed:

cycle 1

(a) Add 2 ul (40 units) RNA ligase (phage T4, New England Biolabs). Incubate at 37° C. for 15 minutes. Heat at 95° C. for 5 minutes, cool to room temperature.

(b) Add 1 ul (3 units) Alkaline Phosphatase (calf intestine, US Biochemicals). Incubate at 37° C. for 30 minutes. Heat at 95° C. for 5 minutes, cool to room temperature.

cycle 2-starting volume is 20 ul (a) Add 10 ul 10 mM AppAp+1 ul RNA ligase. Incubate at 37° C. for 30 minutes. Heat at 95° C. for 5 minutes, cool to room temperature.

(b) same as cycle 1

Insoluble coagulated protein debris was removed by pelleting at 12,000 g for 1 min. The reaction mixture supernatant was analyzed by TLC using the Sure-Check ™ Oligonucleotide Kit (US Biochemicals). The only oligonucleotide product visible on the TLC plate was the desired oligonucleotide product ApApCpApA; i.e., no n−2, n−1, n+1, n+2, etc. products were formed. This experiment demonstrates that AppA does not participate in the RNA ligase coupling reaction, due to its slow coupling rate relative to AppAp. This experiment also demonstrates that coupling times with efficiencies approaching 100% can be achieved in 15 minutes under these experimental conditions. This is attributable to the nucleotide 3',5'-ADP present in the AppAp preparation, which prevents covalent inactivation of RNA ligase. The final yield of oligonucleotide product approached 100%.

EXAMPLE 3

Synthesis of (ApApC)-pApA

The following solution was placed in a total volume of 30 µl in an ependorf tube: 50 mM Tris-Cl, pH 8.0, 10 mM MgCl$_2$, 10 mM DTT, 0.1% TRITON X-100, 1 mM ApApC primer, 5 mM AppAp. The following procedures were performed:

cycle 1

(a) Add 1 ul (20 units) RNA ligase (phage T4, New England Biolabs). Incubate at 37° C. for 1 hour. Heat at 95° C. for 5 minutes, cool to room temperature.

(b) Add 1 ul (0.03 units) Nucleotide Pyrophosphatase (snake venom, Sigma Chemical Co. P7383). Incubate at 37° C. for 30 minutes. Heat at 95° C. for 5 minutes, cool to room temperature.

(c) Add 1 ul (3 units) Alkaline Phosphatase (calf intestine, US Biochemicals). Incubate at 37° C. for 30 minutes. Heat at 95° C. for 5 minutes, cool to room temperature.

cycle 2

(a) Add 10 ul 10 mM AppAp+1 ul RNA ligase. Incubate at 37° C. for 5 hours. Heat at 95° C. for 5 minutes, cool to room temperature.

(b) same as cycle 1

(c) same as cycle 1

Insoluble coagulated protein debris was removed by pelleting at 12,000 g for 5 min. The reaction mixture supernatant was analyzed by TLC using the Sure-Check ™ Oligonucleotide Kit (US Biochemicals). This revealed pure ApApCpApA product with no visible n−1 or initial primer present. The yield of final product was about 90% of the initial primer.

EXAMPLE 4

Synthesis of (ApApC)-pApA

The following solution was placed in a total volume of 30 ul in an ependorf tube: 50 mM Tris-Cl, pH 8.0, 10 mM MgCl$_2$, 10 mM DTT, 0.1% TRITON X-100, 1 mM ApApC primer, 5 mM AppAp. The following procedures were performed:

cycle 1

Performed identically to cycle 1 of example 3.

cycle 2

(a) Add 1.5 ul 100 mM ATP+3 ul 50 mM 3'5'-ADP+0.1 units Inorganic Pyrophosphatase+1 ul RNA ligase. Incubate at 37° C. for 5 hours. Heat at 95° C. for 5 minutes, cool to room temperature.

(b) same as cycle 1 of example 3

(c) same as cycle 1 of example 3

Insoluble coagulated protein debris was removed by pelleting at 12,000 g for 5 min. The reaction mixture supernatant was analyzed by TLC using the Sure-Check ™ Oligonucleotide Kit (US Biochemicals). This revealed nearly pure ApApCpApA product with no visible n−1 or initial primer present. The yield of final product was about 90% of the initial primer.

EXAMPLE 5

Synthesis of dApdA

The oligonucleotide dApdA was synthesized by initially synthesizing the oligonucleotide (ApApC)-pdApdA using the initial primer ApApC and two coupling cycles with the activated nucleotide AppdAp. Synthesized oligodeoxyribonucleotide dApdA was cleaved from the initial primer using RNase treatment.

The following solution was placed in a total volume of 30 ul in an ependorf tube: 50 mM Tris-Cl, pH 8.0, 10 mM MgCl$_2$, 10 mM DTT, 0.1% TRITON X-100, 1 mM ApApC primer, 5 mM AppdAp. The following procedures were performed:

cycle 1

(a) Add 1 ul (20 units) RNA ligase (phage T4, New England Biolabs). Incubate at 37° C. for 3 hours. Heat at 95° C. for 5 minutes, cool to room temperature.

(b) Add 1 ul (0.03 units) Nucleotide Pyrophosphatase (snake venom, Sigma Chemical Co. P7383). Incubate at 37° C. for 30 minutes. Heat at 95° C. for 5 minutes, cool to room temperature.

(c) Add 1 ul (3 units) Alkaline Phosphatase (calf intestine, US Biochemicals). Incubate at 37° C. for 30 minutes. Heat at 95° C. for 5 minutes, cool to room temperature.

cycle 2

(a) Add 10 ul 10 mM AppdAp+1 ul RNA ligase. Incubate at 37° C. for 20 hours. Heat at 95° C. for 5 minutes, cool to room temperature.

(b) same as cycle 1

(c) same as cycle 1

Insoluble coagulated protein debris was removed by pelleting at 12,000 g for 5 min. The reaction mixture supernatant was analyzed by TLC using the Sure-Check ™ Oligonucleotide Kit (US Biochemicals). This revealed pure ApApCpdApdA product with no visible n−1 or initial primer present. The yield of final product was about 90% of the initial primer. Cleavage of the synthesized oligodeoxyribonucleotide dApdA from the oligonucleotide product was performed by adding 100 ng RNase A (bovine pancreas, US Biochemicals) to 4 ul oligonucleotide product and incubating at 37° C. for 1 hour. dApdA product was analyzed and purified from nucleosides and ApApCp using silica TLC in the mobile phase isobutyric acid: concentrated ammonium hydroxide:water at 66:1:33 containing 0.04% EDTA.

EXAMPLE 6

Synthesis of (ApApC)-pApA

The following solution was placed in a total volume of 30 ul in an ependorf tube: 50 mM Tris-Cl, pH 8.0, 10 mM MgCl$_2$, 10 mM DTT, 0.1% TRITON X-100, 1 mM ApApC primer, 5 mM AppAp containing 10% glycerol as a preservative. The solution was overlaid with 50 ul light mineral oil to prevent evaporation. The following procedures were performed:

cycle 1

(a) Add 1 ul (20 units) RNA ligase (phage T4, New England Biolabs)+0.5 ul (0.2 units) Inorganic Pyrophosphatase (Sigma, yeast)+0.5 ul (0.025 units) 5'-Nucleotidase (Sigma, snake venom). Incubate at 37+ C. for 1 hour. Heat at 95° C. for 5 minutes, cool to room temperature.

(b) Add 1 ul (0.03 units) Nucleotide Pyrophosphatase (Sigma P7383, snake venom). Incubate at 37° C. for 30 minutes. Heat at 95° C. for 5 minutes, cool to room temperature.

(C) Add 1 ul (3 units) Alkaline Phosphatase (calf intestine, US Biochemicals)+0.5 ul (0.05 units) Nucleoside Phosphorylase (Sigma). Incubate at 37+ C. for 30 minutes. Heat at 95° C. for 5 minutes, cool to room temperature.

cycle 2

(a) Add 10 ul 10 mM AppAp+1 ul (20 units) RNA ligase. Incubate at 37° C. for 5.5 hours. Heat at 95° C. for 5 minutes, cool to room temperature.

(b) same as cycle 1

(c) same as cycle 1

Insoluble coagulated protein debris was removed by adding 5 ug proteinase K (Sigma) and incubating at 60° C. for 5 minutes. This treatment removed most of the debris. The proteinase K was heat inactivated at 95° C. for 5 minutes, then cooled to room temperature. Mineral oil was removed with a pipettor. Residual mineral oil was removed by adding 100 ul chloroform, vortexed vigorously, and centrifuged at 12,000 g for 1 minute to separate the phases. The chloroform extraction also removed protein from the aqueous phase, which appeared between the two phases. The upper aqueous phase was collected by pipettor and was analyzed by TLC using the SureCheck ™ Oligonucleotide Kit (US Biochemicals). This revealed pure ApApCpApA product with no visible n−1 or initial primer present. The yield of final product was about 90% of the initial primer.

EXAMPLE 7

Synthesis of (ApApC)-pApA

The following solution was placed in a total volume of 30 ul in an ependorf tube: 50 mM Tris-Cl, pH 8.0, 10 mM MgCl$_2$, 10 mM DTT, 0.1% TRITON X-100, 1 mM ApApC primer, 5 mM AppAp. The following procedures were performed:

cycle 1

(a) Add 1 ul (20 units) RNA ligase (phage T4, New England Biolabs). Incubate at 37+ C. for 1 hour. Add 1 ug Proteinase K (Sigma), incubate at 60° C. for 5 minutes, heat at 95° C. for 5 minutes to inactivate protease, and cool to room temperature.

(b) Add 1 ul (0.03 units) Nucleotide Pyrophosphatase (snake venom, Sigma Chemical Co. P7383). Incubate at 37+ C. for 30 minutes. Add 1 ug Proteinase K (Sigma), incubate at 60° C. for 5 minutes, heat at 95° C. for 5 minutes to inactivate protease, and cool to room temperature.

(c) Add 1 ul (3 units) Alkaline Phosphatase (calf intestine, US Biochemicals). Incubate at 37° C. for 30 minutes. Add 1 ug Proteinase K (Sigma), incubate at 60° C. for 5 minutes, heat at 95° C. for 5 minutes to inactivate protease, and cool to room temperature.

cycle 2

(a) Add 10 ul 10 mM AppAp+1 ul (20 units) RNA ligase. Incubate at 37° C. for 5.5 hours. Add 1 ug Proteinase K (Sigma), incubate at 60° C. for 5 minutes, heat at 95° C. for 5 minutes to inactivate protease, and cool to room temperature.

(b) same as cycle 1

(c) Add 1 ul (3 units) Alkaline Phosphatase (calf intestine, US Biochemicals). Incubate at 37° C. for 30 minutes.

The use of Proteinase K for the inactivation of enzymes after each step prevented the accumulation of insoluble coagulated protein debris. The reaction mixture supernatant was analyzed by TLC using the SureCheck ™ Oligonucleotide Kit (US Biochemicals). This revealed pure ApApCpApA product with no visible n−1 or initial primer present. The yield of final product was about 90% of the initial primer.

EXAMPLE 8

Synthesis of (ApApC)-pApA

The following solution was placed in a total volume of 30 ul in an ependorf tube: 50 mM Tris-Cl, pH 8.0, 10 mM MgCl$_2$, 10 mM DTT, 0.1% TRITON X-100, 1 mM ApApC primer, 5 mM AppAp, containing 10% dimethylsulfoxide to inhibit base pairing. The synthesis procedure was identical to Example 3. TLC revealed pure ApApCpApA product with no visible n−1 or initial primer present. The yield of final product was about 90% of the initial primer.

EXAMPLE 9

Synthesis of (ApApC)-pApA

The following solution was placed in a total volume of 30 ul in an ependorf tube: 50 mM Tris-Cl, pH 8.0, mM MgCl$_2$, 10 mM DTT, 0.1% TRITON X-100, 1 mM ApApC primer, 5 mM AppAp, 10 uM Vanadyl Ribonucleoside Complexes (to inhibit any contaminating RNases). The synthesis procedure was identical to Example 3. TLC revealed pure ApApCpApA product with no visible n−1 or initial primer present. The yield of final product was about 90% of the initial primer.

EXAMPLE 10

Synthesis of (ApApC)-pApA

The following solution was placed in a total volume of 30 ul in an ependorf tube: 50 mM Tris-Cl, pH 8.0, 10 mM MgCl$_2$, 10 mM DTT, 0.1% TRITON X-100, 1 mM ApApC primer, and 5 mM AppAp. The following procedures were performed:

cycle 1

(a) Add 1 ul (20 units) RNA ligase (phage T4, New England Biolabs)+1 ul 3 mM sodium pyrophosphate+1 ul 300 mM glucose+0.2 units hexokinase (yeast, Sigma). Incubate at 37+ C. for 1 hour. Heat at 95° C. for 5 minutes, cool to room temperature.

(b) Add 1 ul (0.03 units) Nucleotide Pyrophosphatase (snake venom, Sigma Chemical Co. P7383). Incubate at 37+ C. for 30 minutes. Heat at 95° C. for 5 minutes, cool to room temperature.

(c) Add 1 ul (3 units) Alkaline Phosphatase (calf intestine, US Biochemicals). Incubate at 37° C. for 30 minutes. Heat at 95° C. for 5 minutes, cool to room temperature.

cycle 2

(a) Add 10 ul 10 mM AppAp+1 ul (20 units) RNA ligase+1 ul 3 mM sodium pyrophosphate+1 ul 300 mM glucose+0.2 units hexokinase. Incubate at 37+ C. for 3.5 hours. Heat at 95° C. for 5 minutes, cool to room temperature.

(b) same as cycle 1

(c) same as cycle 1

Insoluble coagulated protein debris was removed by pelleting at 12,000 g for 5 min. The reaction mixture supernatant was analyzed by TLC using the SureCheck ™ Oligonucleotide Kit (US Biochemicals). This revealed nearly pure ApApCpApA product with slight n−1 side product.

EXAMPLE 11

One Pot Synthesis of ApApC-pApA with TAP

The following solution was placed in a total volume of 30 ul in an ependorf tube: 50 mM BES, pH 7.0, 10 mM MgCl$_2$, 10 mM DTT, 0.1% TRITON X-100, 1 mM ApApC primer, 5 mM AppAp. The following procedures were performed:

cycle 1

(a) Add 2 ul (40 units) RNA Ligase (phage T4, New England Biolabs). Incubate at 37° C. for 2 hours. Heat at 95° C. for 5 minutes, cool to room temperature.

(b) Add 1 ul (3 units) Alkaline Phosphatase (calf intestine, US Biochemicals)+1 ul (2 units) Tobacco Acid Pyrophosphatase (Sigma). Incubate at 37° C. for 3.5 hours. Heat at 95° C. for 5 minutes, cool to room temperature.

cycle 2

(a) Add 10 ul 10 mM AppAp+1 ul RNA Ligase. Incubate at 37° C. for 30 minutes. Heat at 95° C. for 5 minutes, cool to room temperature.

(b) same as cycle 1

Insoluble coagulated protein debris was removed by pelleting at 12,000 g for 1 min. The reaction mixture supernatant was analyzed by TLC using the Sure-Check TM Oligonucleotide Kit (US Biochemicals). The only oligonucleotide product visible on the TLC plate was the desired oligonucleotide product ApApCpApA. The final yield of oligonucleotide product was nearly 100%.

EXAMPLE 12

Synthesis of ApApC-pdApdA Using TdT+ddATP Capping

The following solution was placed in a total volume of 30 ul in an ependorf tube: 50 mM Tris-Cl, pH 8.0, 10 mM MgCl$_2$, 10 mM DTT, 0.1% TRITON X-100, 1 mM ApApC primer, 5 mM AppdAp. The following procedures were performed:

cycle 1

(a) Add 1 ul (20 units) RNA Ligase (phage T4, New England Biolabs). Incubate at 37° C. for 3 hours. Heat at 95° C. for 5 minutes, cool to room temperature.

(b) Add 1 ul Terminal deoxynucleotidyl Transferase (TdT, USB, 17 units/ul)+3 ul 5 mM dideoxyadenosine 5'-triphosphate. Incubate at 37° C. for 2.5 hours. Add 1 ug Proteinase K, incubate at 60° C. for 15 minutes, heat at 95° C. for 5 min, cool to room temperature.

(c) Add 1 ul (0.03 units) Nucleotide Pyrophosphatase (snake venom, Sigma Chemical Co. P7383). Incubate at 37° C. for 30 minutes. Heat at 95° C. for 5 minutes, cool to room temperature.

(d) Add 1 ul (3 units) Alkaline Phosphatase (calf intestine, US Biochemicals). Incubate at 37° C. for 30 minutes. Heat at 95° C. for 5 minutes, cool to room temperature.

cycle 2

(a) Add 10 ul 10 mM AppdAp+1 ul RNA Ligase. Incubate at 37° C. for 15 hours. Heat at 95° C. for 5 minutes, cool to room temperature.

(b) same as cycle 1
(c) same as cycle 1
(d) same as cycle 1

Insoluble coagulated protein debris was removed by pelleting at 12,000 g for 5 min. The reaction mixture supernatant was analyzed by TLC using the Sure-Check TM Oligonucleotide Kit (US Biochemicals). The only oligonucleotide product visible was the desired product ApApCpdApdA. The yield of final product was about 90% of the initial primer.

EXAMPLE 13

Synthesis of ApApC-pApA Using Enzyme-Solid Support Matrix

The following solution was placed in a total volume of 30 ul in an ependorf tube: 50 mM Tris-Cl, pH 8.0, 10 mM MgCl$_2$, 10 mM DTT, 0.1% TRITON X-100, 1 mM ApApC primer, 5 mM AppAp. The following procedures were performed:

cycle 1

(a) Add 1 ul (20 units) RNA Ligase (phage T4, New England Biolabs). Incubate at 37° C. for 1 hour. Heat at 95° C. for 5 minutes, cool to room temperature.

(b) Add 1 ul (0.03 units) Nucleotide Pyrophosphatase (snake venom, Sigma Chemical Co. P7383). Incubate at 37° C. for 30 minutes. Heat at 95° C. for 5 minutes, cool to room temperature.

(C) Add 6 ul Alkaline Phosphatase-Acrylic Beads (calf intestine, Sigma Chemical Co.). Incubate at 37° C. for 2.5 hours with occassional mixing. Remove CIAP-acrylic beads by briefly pelleting. Heat supernatant at 95° C. for 5 minutes to remove any residual CIAP leakage, cool to room temperature.

cycle 2

(a) Add 10 ul 10 mM AppAp+1 ul RNA Ligase. Incubate at 37° C. for 2 hours. Heat at 95° C. for 5 minutes, cool to room temperature.

(b) same as cycle 1

(c) same as cycle 1, except skip the heat inactivation

Insoluble coagulated protein debris was removed by pelleting at 12,000 g for 5 min. The reaction mixture supernatant was analyzed by TLC using the Sure-Check TM Oligonucleotide Kit (US Biochemicals). This revealed a mixture of approximately 50% ApApCpA and 50% ApApCpApA oligonucleotide product. The n−1 failure sequence was due to the incomplete 3'-dephosphorylation of the oligonucleotide in the first cycle. This example demonstrates that the enzymes can be covalently attached to a solid matrix in the One Pot method.

Example 14

The method of the invention can be used for synthesizing oligonucleotide mixtures in which two or more different bases are used at a particular position. This technique is known in the art as "wobbling" and is useful in hybridization applications of an oligonucleotide to a DNA library based on amino acid sequence. Wobbling is performed by adding a mixture of blocked nucleotide substrates instead of a single blocked nucleotide substrate during the RNA ligase step of one cycle. The relative amounts of the blocked nucleotides used is selected to balance out differences in coupling rate. For example, if a 50:50 mix of A and G is desired, a mixture of the nucleotide substrates AppAp and AppGp would be added during the RNA ligase step of the appropriate reaction cycle. If the reactivities of AppAp and AppGp are equal, the substrates would be used in equal amounts.

I claim:

1. A method for synthesizing an oligonucleotide of defined sequence, comprising the steps of:

(a) combining (1) an oligonucleotide primer and (2) a blocked nucleotide or a blocked nucleotide precursor that forms a blocked nucleotide in situ, in a reaction mixture in the presence of a chain extending enzyme effective to couple the blocked nucleotide to the 3'-end of the oligonucleotide primer such that a primer-blocked nucleotide product is formed, said blocked nucleotide comprising a nucleotide to be added to form part of the defined sequence and a blocking group attached to the nucleotide effective to prevent the addition of more than one blocked nucleotide to the primer;

(b) inactivating the chain extending enzyme;

(c) removing the blocking group from the 3'-end of the primer-blocked nucleotide product to form a primer-nucleotide product, whereby the reaction mixture contains unreacted starting materials, primer-nucleotide product and reaction by-products;

(d) converting any unreacted blocked nucleotide in the reaction mixture to an unreactive form which is less active as a substrate for the chain extending enzyme than the blocked nucleotide;

(e) repeating a cycle of steps (a) through (d) using the primer-nucleotide product of step (c) as the primer of step (a) for sufficient cycles to obtain a synthesized oligonucleotide of the defined sequence; and (f) cleaving the initial primer used in the first cycle from synthesized oligonucleotide.

2. A method according to claim 1, wherein the initial primer contains a 3' terminal ribose base, and the synthesized oligonucleotide does not contain any ribose bases, and the synthesized oligonucleotide is cleaved from the initial primer using RNase or alkali.

3. A method according to claim 1, wherein the initial primer contains a 3' terminal deoxyuridine base, and the synthesized oligonucleotide is cleaved from the initial primer by treatment with Uracil DNA Glycosylase followed by alkaline treatment.

4. A method according to claim 1, wherein the synthesized oligonucleotide contains phosphorothioate internucleotidic linkages, and the initial primer does not contain phosphorothioate internucleotidic linkages, and the synthesized oligonucleotide is cleaved from the initial primer by a nuclease which is unable to cleave at phosphorothioate internucleotidic linkages.

5. A method according to claim 1, wherein the initial primer contains the recognition site for a ribozyme and the synthesized oligonucleotide does not contain this recognition site, and the initial primer is cleaved from the synthesized oligonucleotide by incubation with the ribozyme.

6. A method according to claim 1, wherein the initial primer contains the recognition site for a restriction endonuclease which is able to cleave single stranded DNA, and the synthesized oligonucleotide does not contain this recognition site, and the initial primer is cleaved from the synthesized oligonucleotide by incubation with this restriction endonuclease.

7. A method according to claim 1, wherein the initial primer is composed of deoxyribose bases and the synthesized oligonucleotide does not contain deoxyribose bases and DNase is added to specifically hydrolyze the initial primer.

8. A method according to claim 1, wherein the initial primer is composed of ribose bases and an oligodeoxyribonucleotide is added which specifically anneals to the initial primer and RNase H is added to specifically hydrolyze the initial primer.

9. A method according to claim 1, wherein the initial primer is composed of ribose bases and an oligoribonucleotide is added which specifically anneals to the initial primer and a double strand specific RNase is added to remove the initial primer.

10. A method according to claim 1, wherein the initial primer is a self-annealing oligoribonucleotide or oligodeoxyribonucleotide which forms double stranded oligonucleotide, and a double strand specific nuclease is added to remove the initial primer.

11. A method according to claim 1, wherein an oligodeoxyribonucleotide is added which specifically anneals to the initial primer and forms double stranded DNA region recognition site for a restriction endonuclease, and a restriction enzyme is added to remove the initial primer.

12. A method according to claim 1, wherein the initial primer contains the modified sugar 2'-O-Methyl Ribose, and the synthesized oligonucleotide does not contain the modified sugar 2'-O-Methyl Ribose, and RNase Alpha is added to cleave the initial primer from the synthesized oligonucleotide.

13. A method according to claim 1, wherein the initial primer contains a base recognized by a base-specific ribonuclease and the initial primer is cleaved from the synthesized oligonucleotide by incubation with the base-specific oligonucleotide.

14. A method according to claim 14, further comprising the step of digesting the initial primer with an enzyme, substantially without digestion of the synthesized oligonucleotide.

15. A method according to claim 1, wherein the initial primer does not contain a 5'-phosphate and cleavage of the initial primer results in a 5'-phosphate on the synthesized oligonucleotide, and wherein the initial primer in hydrolyzed with a 5' to 3' Exonuclease which is active on 5'-hydroxyl oligonucleotides and substantially inactive on 5'-phosphate oligonucleotides.

16. A method according to claim 14, wherein the cleavage of the initial primer is performed prior to the removal of the blocking group from the synthesized oligonucleotide and results in a 3'-hydroxyl on the initial primer, and wherein the initial primer is hydrolized by incubating with a 3' to 5' Exonuclease which is active on 3' hydroxyl oligonucleotides and substantially inactive on the blocked synthesized oligonucleotide.

17. A method according to claim 14, wherein the cleavage of the initial primer is performed prior to the removal of the blocking group from the synthesized oligonucleotide and results in a 5'-hydroxyl on the synthesized oligonucleotide and a 5'-phosphate on the primer, and wherein the primer is hydrolyzed with a 5' to 3' Exonuclease which is active on 5'-phosphate oligonucleotides and substantially inactive 5'-hydroxyl oligonucleotides.

18. A method according to claim 1, wherein each cycle set forth in step (e) is carried out without prior separation of the primer-nucleotide product of the preceding cycle from the remainder of the reaction mixture.

* * * * *

UNITED STATES PATENT AND TRADEMARK OFFICE
CERTIFICATE OF CORRECTION

| | | |
|---|---|---|
| PATENT NO. | : 5,436,143 | Page 1 of 1 |
| APPLICATION NO. | : 07/995791 | |
| DATED | : July 25, 1995 | |
| INVENTOR(S) | : Edward Hyman | |

It is certified that error appears in the above-identified patent and that said Letters Patent is hereby corrected as shown below:

On the Title page,

Item [74], "Oppendahl" should read -- Oppedahl --

Signed and Sealed this

Eighteenth Day of May, 2010

David J. Kappos
*Director of the United States Patent and Trademark Office*